United States Patent
Wilcox et al.

(10) Patent No.: US 11,529,340 B2
(45) Date of Patent: Dec. 20, 2022

(54) COMBINATION FOR TREATING PAIN

(71) Applicants: Regents of the University of Minnesota, Minneapolis, MN (US); George Latimer Wilcox, Minneapolis, MN (US); Daniel John Bruce, Minneapolis, MN (US); Carolyn Ann Fairbanks, Minneapolis, MN (US); Philip S. Portoghese, Minneapolis, MN (US); Eyup Akgun, Minneapolis, MN (US)

(72) Inventors: George Latimer Wilcox, Minneapolis, MN (US); Daniel John Bruce, Minneapolis, MN (US); Carolyn Ann Fairbanks, Minneapolis, MN (US); Philip S. Portoghese, Minneapolis, MN (US); Eyup Akgun, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 716 days.

(21) Appl. No.: 16/088,000

(22) PCT Filed: Mar. 22, 2017

(86) PCT No.: PCT/US2017/023647
§ 371 (c)(1),
(2) Date: Sep. 24, 2018

(87) PCT Pub. No.: WO2017/165558
PCT Pub. Date: Sep. 28, 2017

(65) Prior Publication Data
US 2020/0289489 A1 Sep. 17, 2020

Related U.S. Application Data

(60) Provisional application No. 62/311,781, filed on Mar. 22, 2016.

(51) Int. Cl.
*A61K 31/451* (2006.01)
*A61P 25/04* (2006.01)
*A61K 31/485* (2006.01)

(52) U.S. Cl.
CPC .......... *A61K 31/451* (2013.01); *A61K 31/485* (2013.01); *A61P 25/04* (2018.01)

(58) Field of Classification Search
CPC ................ A61K 31/451; A61K 31/485; A61K 2300/00; A61P 25/04
See application file for complete search history.

(56) References Cited

U.S. PATENT DOCUMENTS

| | | |
|---|---|---|
| 4,816,586 A | 3/1989 | Portoghese |
| 5,886,001 A | 3/1999 | Schmidhammer |
| 6,177,438 B1 | 1/2001 | Nagase et al. |
| 6,277,859 B1 | 8/2001 | Nagase et al. |
| 6,609,682 B2 | 8/2003 | Rogers et al. |
| 9,981,043 B2 | 5/2018 | Portoghese et al. |
| 10,464,941 B2 | 11/2019 | Portoghese et al. |
| 2004/0101582 A1 | 5/2004 | Wolicki |
| 2004/0152689 A1 | 8/2004 | Chen |
| 2007/0208028 A1 | 9/2007 | Conn et al. |
| 2009/0233841 A1 | 9/2009 | Portoghese et al. |
| 2011/0245287 A1 | 10/2011 | Holaday et al. |

FOREIGN PATENT DOCUMENTS

| | | |
|---|---|---|
| EP | 0661283 A1 | 7/1995 |
| EP | 0663401 A1 | 7/1995 |
| WO | 2005075455 A2 | 8/2005 |
| WO | 2005117589 A1 | 12/2005 |
| WO | 2006073396 A1 | 7/2006 |
| WO | 2007017764 A2 | 2/2007 |
| WO | 2012109464 A2 | 8/2012 |
| WO | 2014124317 A1 | 8/2014 |

OTHER PUBLICATIONS

Zhang, S, et al., "A bivalent ligand (KMN-21) antagonist for μ/K heterodimeric opioid receptors", Biorg Med Chem Lett 19, 6978-6980 (2009).

Zhang, Y, et al., "Homology modeling and molecular dynamics simulations of the mu opioid receptor in a membrane-aqueous system", ChemBioChem 6, 853-859 (2005).

Zhang, Y, et al., "Specific Cross-Linking of Lys233 and Cys235 in the Mu Opioid receptor by a Reporter Affinity Label", Biochemistry 44, 2271-2275 (2005).

Zheng, Y, et al., "Induced association of mu opioid (MOP) and type 2 cholecystokinin (CCK2) receptors by novel bivalent ligands.", J Am Chem 52(2), 247-258 (2009).

Chung, C, et al., "Analgesic properties of loperamide differ following systemic and local administration to rats after spinal nerve injury", Eur J Pain 16, 1021-1032 (2012).

Dehaven-Hudkins, D, et al., "Loperamide (ADL 2-1294), an Opioid Antihyperalgesic Agent with Peripheral Selectivity", Journal of Pharmacology and Experimental Therapeutics 289(1), 494-502 (1999).

Iwaszkiewicz, K, et al., "Development of an Effective Topical Liposomal Formulation for Localized Analgesia and Antiinflammatory Actions in the Complete Freund's Adjuvant Rodent Model of Acute Inflammatory Pain", Pain Physician 17, E719-E735 (2014).

Joris, J, et al., "Opioid analgesia at peripheral sites: a target for opioids released during stress and inflammation?", Anesth Analg 66(12), 1277-1281 (1987).

Kolesnikov, Y, et al., "Topical methadone and meperidine analgesic synergy in the mouse", Eur J Pharmacol 63 (8), 61-64 (2010).

(Continued)

*Primary Examiner* — Alicia L Otton
(74) *Attorney, Agent, or Firm* — Viksnins Harris Padys Malen LLP

(57) ABSTRACT

The invention provides compounds, compositions, and methods for treating pain.

2 Claims, 18 Drawing Sheets

(56) References Cited

OTHER PUBLICATIONS

Levine, J., et al., "Involvement of the mu-opiate receptor in peripheral analgesia", Neuroscience 32(3), 571-575 (1989).
Menendez, L., et al., "Analgesic effects of loperamide in bone cancer pain in mice", Pharmacology, Biochemistry and Behavior 81, 11-121 (2005).
Nozaki-Taguchi, N., et al., "Characterization of the Antihyperalgesic Action of a Novel Peripheral Mu-opioid Receptor Agonist-Loperamide", Anesthesiology 90, 225-234 (1999).
Patent Cooperation Treaty, International Searching Authority, Search Report and Written Opinion for PCT/US2017/023647, 17 pages, dated Jun. 8, 2017.
Portoghese, P., et al., "Application of the message-address concept in the design of highly potent and selective non-peptide .delta. opioid receptor antagonists", J Med Chem 31(2), 281-282 (1988).
Schuster, DJ., "Ligand requirements for involvement of PKCε in synergistic analgesic interactions between spinal μ and δ opioid receptors", Br J Pharmacol. 172(2) 642-653 (2015).
Shook, J., et al., "Antidiarrheal properties of supraspinal mu and delta and peripheral mu, delta and kappa opioid receptors: inhibition of diarrhea without constipation", J Pharmacol Exp Ther 249(1), 83-90 (1989).
Stein, C., "Peripheral mechanisms of opioid analgesia", Anesth Analg 76(1), 182-191 (1993).
Stone, L., et al., "Morphine and clonidine combination therapy improves therapeutic window in mice: synergy in antinociceptive but not in sedative or cardiovascular effects", PLoS One 9(10), e109903 (2010).
Aceto, M., et al., "MDAN-21: A Bivalent Opioid Ligand Containing mu-Agonist and Delta-Antagonist Pharmacophores and Its Effects in Rhesus Monkeys", International Journal of Medicinal Chemistry 1-6 (2012).
Akgun, E., et al., "Induction of heterodimerization of mu opioid peptide (MOP) and type-2 cholecystokinin (CCK2) receptor by novel bivalent ligands", Drugs Fut 33 (Suppl. A): XXth Int Symp Med Chem, p. 152 (Aug 31-Sep. 4, Vienna) (2008).
Akgun, E., et al., "Inhibition of Inflammatory and Neuropathic Pain by Targeting a Mu Opioid Receptor/Chemokine Receptor5 Heteromer (MOR-CCR5).", J Med Chem 58(21), 8647-8657 (2015).
Akgun, Eyup, et al., "Ligands that interact with putative MOR-mGluR5 heteromer in mice with inflammatory pain produce potent antinociception", PNAS vol. 110 (28), 11595-11599 (2013).
Bhushan, R., et al., "A Bivalent Ligand (KDN-21) Reveals Spinal δ and κ Opioid Receptors Are Organized as Heterodimers That Give Rise to δ1 and κ2 Phenotypes. Selective Targeting of δ-κ Heterodimers", J Med Chem 47, 2969-2972 (2004).
Carey, FA. Organic Chemistry 6th Ed. McGraw Hill., chapter 1, p. 9. (2006).
Cataldo, G., et al., "Bivalent ligand MCC22 potently attenuates nociception in a murine model of sickle cell disease", Pain 159, 1382-1391 (2018).
Chen, C., et al., "Heterodimerization and cross-desensitization between the mu-opioid receptor and the chemokine CCR5 receptor", Eur J Pharmacol 483, 175-186 (2004).
Cherny, N., et al., "Opioid responsiveness of cancer pain syndromes caused by neuropathic or nociceptive mechanisms: a combined analysis of controlled, single-dose studies", Neurology 44, 857-861 (1994).
Daniels, D., et al., "A Bivalent Ligand (KDAN-18) Containing δ-Antagonist and κ-Agonist Pharmacophores Bridges δ2 and κ1 Opioid Receptor Phenotypes", J Med Chem 48, 1713-1716 (2005).
Daniels, D., et al., "Opioid-induced tolerance and dependence in mice is modulated by the distance between pharmacophores in a bivalent ligand series", Proc Natl Acad Sci 102(52), 19208-19213 (2005).
Fischer, Bradford D., et al., "Increased efficacy of μ-opioid agonist-induced antinociception by metabotropic glutamate receptor antagonists in C57BL/6 mice: comparison with (−)-6-phosphonomethyl-deca-hydroisoquinoline-3-carboxylic acid (LY235959)", Psychopharmacology 198, 271-278 (2008).
Gabra, Bichoy H., et al., "mGluR5 antagonists that block calcium mobilization in vitro also reverse (S)-3,5-DHPG-induced hyperalgesia and morphine antinociceptive tolerance in vivo", Brain Research 1187, 58-66 (2008).
Gasparini, F., et al., "[(3)H]-M-MPEP, a potent, subtype-selective radioligand for the metabotropic glutamate receptor subtype 5", Bioorg Med Chem Lett 12 (3), 407-409 (2002).
Guasti, L., et al., "Minocycline treatment inhibits microglial activation and alters spinal levels of endocannabinoids in a rat model of neuropathic pain", Mol Pain 5, 35, 10 pages (2009).
Guo, Y., et al.,"The role of glutamate and its receptors in mesocorticolimbic dopaminergic regions in opioid addiction", Neurosci Biobehav Rev 33 (6), 864-873 (2009).
Heinrich, P., et al., "Interleukin-6-type cytokine signalling through the gp130/Jak/STAT pathway", Biochem J 334, 297-314 (1998).
Imamura, S., et al., "Discovery of a Piperidine-4-carboxamide CCR5 Antagonist (TAK-220) with Highly Potent Anti-HIV-1 Activity", J Med Chem 49(9), 2784-2793 (2006).
Jorgensen, W., et al., "Comparison of simple potential functions for simulating liquid water", J Chem Phys 79, 926-935 (1983).
Kawai, K., et al., "Design, synthesis, and structure-activity relationship of novel opioid κ-agonists", Bioorganic & Medicinal Chemistry 16, 9188-9201 (2008).
Khasabova, I., et al., "Cannabinoid Type-1 Receptor Reduces Pain and Neurotoxicity Produced by Chemotherapy", J Neurosci 32(20), 7091-7101 (2012).
Kondru, R., et al., "Molecular interactions of CCR5 with major classes of small-molecule anti-HIV CCR5 antagonists", Mol Pharmacol 73, 789-800 (2008).
Le Naour, M., et al., "Bivalent Ligands that Target μ Opioid (MOPP) and Cannabinoid1 (CB1) Receptors are Potent Analgesics Devoid of Tolerance", J Med Chem 56, 5505-5513 (2013).
Le Naour, M., et al., "Bivalent Ligands That Target μ Opioid (MOP) and Cannabinoid1 (CB1) Receptors Are Potent Analgesics Devoid of Tolerance.", J Med Chem 56(13), 5505-5513 (2013).
Lee, Cynthia Wei-Sheng, et al., "Pharmacological Profiles of Oligomerized μ-Opioid Receptors", Cells 2, 689-714 (2013).
Li, G., et al., "Design, Synthesis, and Biological Evaluation of 6a- and 6B-N-Heterocyclic Substituted Naltrexamine Derivatives as μ Opiod receptor Selective Antagonists", J Med Chem 52, 1416-1427 (2009).
Manglik, A., et al., "Crystal structure of the μ-opioid receptor bound to a morphinan antagonist", Nature 485, 321-326 (2012).
McCurdy, C., et al., "Naphthalene Dicarboxaldehyde as an Electrophilic Fluorogenic Moiety for Affinity Labeling Application to Opioid receptor Affinity Labels with Greatly Improved Fluorogenic Properties", Journal of Medicinal Chemistry 45(14), 2887-2890 (2002).
Nishikawa, M., et al., "Analysis of Binding Sites for the New Small-Molecule CCR5 Antagonist TAK-220 on Human CCR5", Antimicrob Agents Chemother 49, 4708-4715 (2005).
Organic Chem Portal, "Synthesis of aryl ethers", 2 pages, accessed Dec. 9, 2018 (2018).
Organic Chem Portal, "Synthesis of carbamates", 3 pages, accessed Dec. 9, 2018 (2018).
Organic Chem Portal, "Synthesis of esters", 2 pages, accessed Dec. 9, 2018 (2018).
Organic Chem Portal, "Synthesis of secondary and tertiary amines", 4 pages, accessed Dec. 9, 2018 (2018).
Padi, S., et al., "Attenuation of rodent neuropathic pain by an orally active peptide, RAP-103, which potently blocks DCR2- and CCR5-mediated monocyte chemotaxis and inflammation", Pain 153, 95-106 (2012).
Patel, S., et al., "Species differences in mGluR5 binding sites in mammalian central nervous system determined using in vitro binding with [18F]F-PEB", Nucl Med Biol 34 (8), 1009-1017 (2007).
Portoghese, P., et al., "Opioid Agonist and Antagonist Bivalent Ligands as Receptor Probes.", Life Sciences, 31 (12 & 13), 1283-1286 (1982).

(56) References Cited

OTHER PUBLICATIONS

Schroder, H., et al., "Allosteric modulation of metabotropic glutamate receptor 5 affects phosphorylation, internalization, and desensitization of the micro-opioid receptor", Neuropharmacology 56 (4), 768-778 (2009).

Singh, M, et al., "Minocycline attenuates HIV-1 infection and suppresses chronic immune activation in humanized NOD/LtsZ-scidIL-2Rγnull mice", Immunology 142, 562-572 (2014).

Smeester, BA, et al., "Targeting putative mu opioid/metabotropic glutamate receptor-5 heteromers produces potent antinociception in a chronic murine bone cancer model.", Eur J Pharmacol 743, 48-52 (2014).

Smith, H, "Treatment Considerations in Painful HIV-Related Neuropathy", Pain Physician 14, E505-524 (2011).

Szeto, G, et al., "Minocycline Attenuates HIV Infection and Reactivation by Suppressing Cellular Activation in Human CD4+ T Cells", J Infect Dis 201, 1132-1140 (2010).

Takashima, K, et al., "Highly Potent Inhibition of Human Immunodeficiency Virus Type 1 Replication by TAK-220, an Orally Bioavailable Small-Molecule CCR5 Antagonist", Antimicrob Agents Chemother 49, 3474-3482 (2005).

Tan, Q, et al., "Structure of the CCR5 chemokine receptor—HIV entry inhibitor Maraviroc complex", Science 341, 1387-1390 (2012).

Tyler, M, et al., "Classics in Chemical Neuroscience: Ketamine", ACS Chem Neurosci 8, 1122-1134 (2017).

Uhelski, M, et al., "Inhibition of anandamide hydrolysis attenuates nociceptor sensitization in a murine model of chemotherapy-induced peripheral neuropathy", J Neurophysiol 113, 1501-1510 (2015).

Weiss, U, "Derivatives of Morphine. I. 14-Hydroxydihydromorphinone", J Am Chem Soc 77(22), 5891-5892 (1955).

Wilson, D, et al., "A continuous fluorescence displacement assay for BioA: an enzyme involved in biotin biosynthesis", Anal Biochem 416, 27-38 (2011).

Xie, Z, et al., "Interaction of Bivalent Ligand KDN21 with Heterodimeric δ-κ Opioid Receptors in Human Embryonic Kidney 293 Cells", Mol Pharmacol 68(4), 1079-1086 (2005).

Yuan, Y, et al., "Design and synthesis of a bivalent ligand to explore the putative heterodimerization of the mu opioid receptor and the chemokine receptor CCR5", Organic & Biomolecular Chemistry 10, 2633 (2012).

Zanos, P, et al., "Ketamine and Ketamine Metabolite Pharmacology: Insights into Therapeutic Mechanisms", Pharmacol Rev 70, 621-660 (2018).

Schramm, C, et al., "Co-administration of delta- and mu-opioid receptor agonists promotes peripheral opioid receptor function", Pain 151, 763-770 (2010).

OMI (100 pmol/mouse) control and antagonized by B-FNA (mu), NTI (delta) and nor-BNI (kappa)

OMI (100 pmol/mouse - 10'): 72.9 ± 11.9; β-FNA (1nmol/mouse - 24 hour): 30.8 ± 3.5: NTI (5 nmol/mouse - 20'): 49.8 ± 7.7; norBNI (5 nmol/mouse - 20'): 61.6 ± 11.0

BOMI (200 pmol/mouse) control and antagonized by B-FNA (mu), NTI (delta) and nor-BNI (kappa)

BOMI (200 pmol/mouse - 10'): 75.3 ± 8.7; β-FNA (1nmol/mouse - 24 hour): 21.9 ± 6.2: NTI (5 nmol/mouse - 20'):44.6 ± 10.3; norBNI (5 nmol/mouse - 20'): 50.5 ± 6.1

OMI (1000 pmol/mouse - 5'): 65.0 ± 12.2; β-FNA (1nmol/mouse - 24 hour): 41.5 ± 13.7: NTI (5 nmol/mouse - 20'): 59.4 ± 13.6; norBNI (2.5 nmol/mouse - 20'): 72.1 ± 10.5

BOMI (50 pmol/mouse - 5'): 75.0 ± 9.5; β-FNA (1nmol/mouse - 24 hour): 20.3 ± 8.7: NTI (5 nmol/mouse - 20'): 72.6 ± 11.4; norBNI (2.5 nmol/mouse - 20'): 70.4 ± 11.4

%MPE drug administered via i.t. administration

%MPE drug administered via i.c.v. administration.

COMBINATION FOR TREATING PAIN

CROSS-REFERENCE TO RELATED APPLICATIONS

This application claims priority to U.S. Provisional Application No. 62/311,781, filed Mar. 22, 2016. The entire content of the application referenced above is hereby incorporated by reference herein.

GOVERNMENT FUNDING

This invention was made with government support under R01 DA015438 and R01 DA001533 awarded by the National Institutes of Health-NIDA. The government has certain rights in the invention.

BACKGROUND OF THE INVENTION

Conservative estimates in the United States alone suggest that approximately 100 million adults suffer from chronic pain, resulting in a societal cost of $600 billion dollars annually in medical costs and lost productivity (Institute of Medicine (US) Committee on Advancing Pain Research, Care and Education, 2011). Despite this, current treatment paradigms for chronic pain are inadequate. Opioid analgesics are among the most powerful and extensively used therapeutics for the treatment of chronic pain, but long-term use is associated with a number of deleterious CNS effects, namely respiratory depression, tolerance, addiction, and hyperalgesia. Additionally, diversion of centrally acting opioids for non-therapeutic use is of major concern in present day North America.

The OTC remedy for diarrhea, loperamide (Lo, trade name Imodium), is a highly efficacious, antidiarrheal, mu-opioid receptor (MOR) agonist that is excluded from the CNS; therefore, it has near zero abuse liability, befitting its OTC approval and availability.

Although prescription opioid analgesics are the gold standard for management of chronic pain, diversion, addiction and respiratory depression constitute a significant problem. Because opioids' addiction potential derives from actions in the mesolimbic dopaminergic system and their respiratory depression from actions in the brainstem, restriction of pharmacodynamic action to the peripheral nervous system represents a simple and effective means to eliminate these liabilities.

Peripheral and topical analgesia targeting MOR is not novel (Joris, J. L., R. Dubner and K. M. Hargreaves *Anesth Analg*, 66(12): 1277-1281, 1987; Levine, J. D. and Y. O. Taiwo, *Neuroscience*, 32(3): 571-575, 1989; and Stein, C., *Anesth Analg*, 76(1): 182-191, 1993); however, the study of analgesic combinations of opioid analgesics in the periphery is rare (Kolesnikov, Y. A., et al., *Eur J Pharmacol*, 63(8): 61-64, 2010).

It has been reported that the delta-opioid receptor (DOR) agonist, oxymorphindole (OMI), synergized with the MOR agonist morphine when administered intrathecally in mice (Schuster, D. J., et al., *Br J Pharmacol*, 72(2): 642-653, 2015). It has also been shown that the synergy between certain analgesics does not generalize to multiple side effects, yielding an analgesic combination with therapeutic windows ranging from 5- to 50-fold larger than either drug given alone (LS Stone et al., *PLoS One*, 9(10):e109903, 2010).

Currently there is a need for additional agents and methods that can be used to treat pain. Ideally, such agents and methods will produce reduced addiction, reduced respiratory depression, and/or fewer unwanted effects on GI transit compared to currently available therapies.

SUMMARY OF THE INVENTION

The invention provides compositions and methods that can be used to treat pain. The compositions and methods of the invention typically produce reduced addiction, reduced respiratory depression, and/or fewer unwanted effects on GI transit compared to currently available therapies.

In one embodiment the invention provides a composition comprising 1) a mu-opioid receptor (MOR) agonist that is excluded from the CNS, 2) a delta-opioid receptor (DOR) agonist, and 3) a pharmaceutically acceptable carrier.

The invention also provides a method for treating pain in an animal (e.g. a human) comprising administering 1) a mu-opioid receptor (MOR) agonist that is excluded from the CNS, and 2) a delta-opioid receptor (DOR) agonist to the animal.

The invention also provides the compound N-benzyloxymorphindole, or a pharmaceutically acceptable salt thereof.

The invention also provides a pharmaceutical composition comprising N-benzyloxymorphindole, or a pharmaceutically acceptable salt thereof, and a pharmaceutically acceptable carrier.

The invention also provides a method for treating pain in an animal (e.g. a human) comprising administering N-benzyloxymorphindole or a pharmaceutically acceptable salt thereof to the animal.

The invention also provides a method for agonizing a delta-opioid receptor comprising contacting the receptor with N-benzyloxymorphindole or a pharmaceutically acceptable salt thereof.

The invention also provides a composition of the invention for use in medical therapy.

The invention also provides a composition of the invention for the prophylactic or therapeutic treatment of pain.

The invention also provides the use of a composition of the invention to prepare a medicament for treating pain in an animal.

The invention also provides the use of a mu-opioid receptor (MOR) agonist that is excluded from the CNS to prepare a medicament for treating pain in an animal in combination with a delta-opioid receptor (DOR) agonist.

The invention also provides the use of a delta-opioid receptor (DOR) agonist to prepare a medicament for treating pain in an animal in combination with a mu-opioid receptor (MOR) agonist that is excluded from the CNS.

The invention also provides N-benzyloxymorphindole, or a pharmaceutically acceptable salt thereof for use in medical therapy.

The invention also provides N-benzyloxymorphindole, or a pharmaceutically acceptable salt thereof for the prophylactic or therapeutic treatment of pain.

The invention also provides the use N-benzyloxymorphindole, or a pharmaceutically acceptable salt thereof to prepare a medicament for treating pain in an animal.

BRIEF DESCRIPTION OF THE FIGURES

FIG. 1a shows antagonism of OMI when administered intracerebroventriclarly. FIG. 1b shows antagonism of BOMI when administered intracerebroventriclarly. FIG. 1c shows antagonism of OMI when administered intrathecally. FIG. 1d shows antagonism of BOMI when administered intrathecally.

FIG. 2a shows calcium mobilization of NTI. FIG. 2b shows calcium mobilization of OMI (4). FIG. 2c shows calcium mobilization of BOMI (6).

FIG. 5a shows centrally-mediated thermal nociceptive responses in the hot water tail flick test. Subjects were given an intrathecal injection of loperamide, OMI, or combination, and post-drug response were analyzed as a % of maximum possible effect, which was used to generate dose-response curves. Note the 10-fold shift in potency for the combination. FIG. 5b shows isobolographic analysis of data from FIG. 5a, demonstrating a synergistic interaction for the combination when compared to the theoretical additive value.

FIG. 7a shows peripherally-mediated thermal nociceptive responses in the Hargreaves assay. Subjects were given an intraplantar injection of loperamide, oxymorphindole or combination and post-drug responses were analyzed as a % of maximum possible effect, which was used to generate dose-response curves. FIG. 7b shows isobolographic analysis of the data from FIG. 7a, demonstrating that the ED50 value of the observed combination (filled circle) is significantly lower than that of the ED50 value that would be expected were the interaction merely additive (white circle); this point is referred to as the theoretical additive point. That difference indicates a synergistic interaction. FIG. 7c shows dose-response curves for intraplantar loperamide, oxymorphindole or combination following CFA-induced inflammation in the hindpaw. Data are analyzed as a % of antihyperalgesia. FIG. 7d shows isobolographic analysis of the data from FIG. 7c, demonstrating that the ED50 value of the observed combination (filled circle) is significantly lower than that of the theoretical additive ED50 value (white circle). The difference indicates a synergistic interaction.

FIG. 8a shows peripherally-mediated thermal nociceptive responses in the Hargreaves assay were assessed. Subjects were given a subcutaneous injection of loperamide, oxymorphindole or combination and post-drug responses were analyzed as a % of maximum possible effect, which was used to generate dose-response curves. FIG. 8b shows isobolographic analysis of the data from FIG. 8a, showing a synergistic interaction compared to the theoretical additive value. FIG. 8c shows dose-response curves for subcutaneous loperamide, oxymorphindole or combination following CFA-induced inflammation in the hindpaw. Data are analyzed as a % of antihyperalgesia. FIG. 8d shows isobolographic analysis of the data from FIG. 8c, demonstrating that the ED50 value of the observed combination (filled circle) is significantly lower than that of the theoretical additive ED50 value (white circle). The interaction is synergistic.

FIG. 9a shows ability of beta-funaltrexamine (β-FNA), an irreversible MOR antagonist, to inhibit OMI-Lo anti-hyperalgesia. Three different doses of β-FNA were given 24 hours before OMI-Lo as an intraplantar injection. FIG. 9b shows ability of naltrindole, a DOR antagonist, to inhibit OMI-Lo anti-hyperalgesia. Increasing doses of naltrindole were given concurrently with 0.3 nmol of OMI-Lo as an intraplantar injection. FIG. 9c shows ability of naloxone methiodide, a peripherally restricted opioid antagonist, to inhibit OMI-Lo anti-hyperalgesia. Increasing doses of naloxone methiodide were given concurrently with 0.3 nmol OMI-Lo as an intraplantar injection. FIGS. 9d, 9e, and 9f show ability of systemic antagonists to block systemic Lo-OMI. Paw withdrawal thresholds were measured using the Hargreaves assay and antagonist data were compared to 0.3 nmol OMI-Lo using one-way ANOVA with Bonferroni's multiple comparison's test.

FIG. 10a shows peripherally-mediated thermal nociceptive responses in the Hargreaves assay were assessed. Subjects were given a topical solution of loperamide, oxymorphindole or their combination on the inflamed hindpaw and post-drug responses were analyzed as a % of anti-hyperalgesia, which was used to generate dose-response curves. FIG. 10b shows isobolographic analysis of the data from FIG. 10a, demonstrating that the ED50 value of the observed combination (filled circle) is significantly lower than that of the theoretical additive ED50 value (white circle). The interaction is synergistic.

FIGS. 11a-11c show mechanical allodynia was induced with a spared nerve injury (SNI) surgery in mice. Pre-surgery baseline responses were taken on the day of surgery, and drug was administered 10 days after surgery. Loperamide (FIG. 11b), oxymorphindole (FIG. 11a), or their combination (FIG. 11c) was given as a subcutaneous injection in the back, and paw withdrawal thresholds were monitored at 30 minute intervals for 3 hours. Peak anti-allodynia occurred 1 hour post-injection and responses returned to post-surgery levels by 3 hours. FIG. 11d shows area under the curve values for each subject were generated, and data was plotted as a dose-response measure.

FIG. 13a shows peripherally-mediated thermal nociceptive responses in the Hargreaves assay were assessed. Subjects were given an intraplantar injection of loperamide, BOMI, or their combination 3-5 days after CFA-induced inflammation and post-drug responses were analyzed as a % of anti-hyperalgesia, which was used to generate dose-response curves. FIG. 13b shows isobolographic analysis of the data from FIG. 13a, showing a synergistic interaction compared to the theoretical additive value. FIG. 13c shows dose-response curves for systemic loperamide, BOMI, or combination following CFA-induced inflammation in the hindpaw. Data are analyzed as a % of antihyperalgesia. FIG. 13d shows isobolographic analysis of the data from FIG. 13c, demonstrating that the ED50 value of the observed combination (filled circle) is significantly lower than that of the theoretical additive ED50 value (white circle). The interaction is synergistic.

DETAILED DESCRIPTION

Figure 1A:
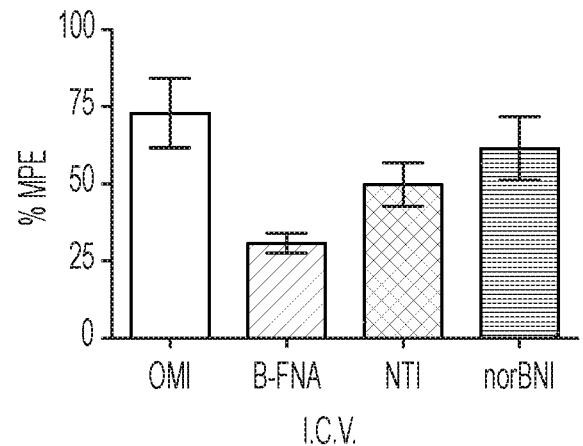
FIGS. 1a-1d show antagonism studies of OMI and BOMI (6) in vivo from Example 2.
Figure 1B:
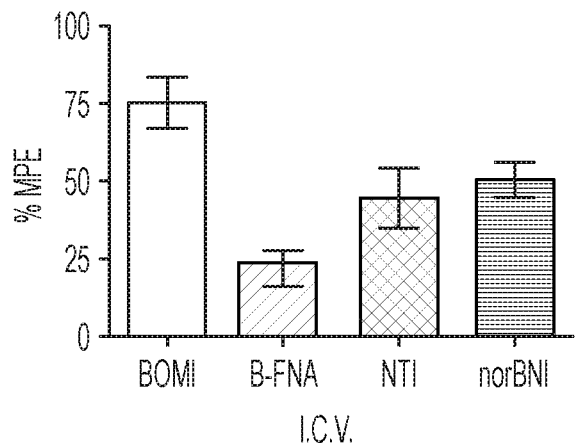
Figure 1C:
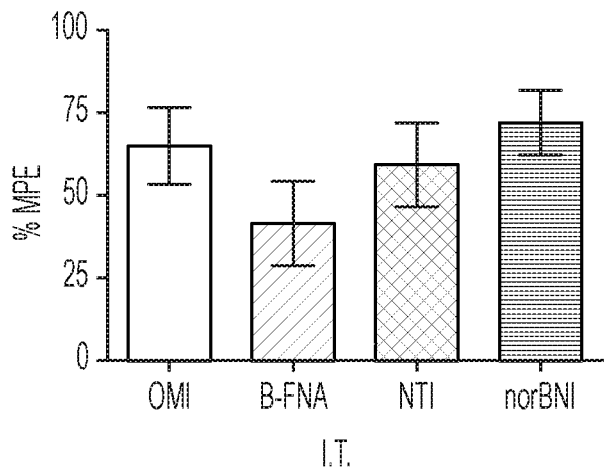
Figure 1D:
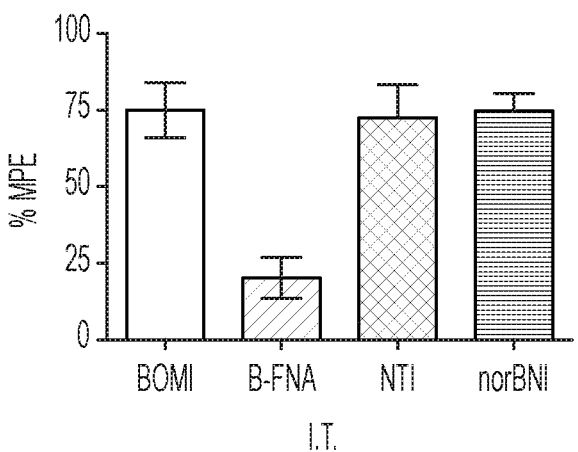

Halo or halogen is fluoro, chloro, bromo, or iodo.

The term "alkyl", by itself or as part of another substituent, means, unless otherwise stated, a straight or branched chain hydrocarbon radical, having the number of carbon atoms designated (i.e., $C_{1-6}$ means one to six carbons). Examples include $C_1$-$C_6$alkyl, ($C_2$-$C_6$)alkyl and ($C_3$-$C_6$) alkyl. Examples of alkyl groups include methyl, ethyl, n-propyl, iso-propyl, n-butyl, t-butyl, iso-butyl, sec-butyl, n-pentyl, n-hexyl, and higher homologs and isomers.

The term "alkylene" by itself or as part of another substituent means a divalent radical derived from an alkane (including straight and branched alkanes), as exemplified by —$CH_2CH_2CH_2CH_2$— and —$CH(CH_3)CH_2CH_2$—.

The term "haloalkyl" refers to an alkyl substituted with one or more halo groups (e.g., ($C_1$-$C_6$)haloalkyl.

The term "alkoxy" refers to an alkyl groups attached to the remainder of the molecule via an oxygen atom ("oxy"). ($C_1$-$C_6$)alkoxy can be methoxy, ethoxy, propoxy, iso-propoxy, butoxy, iso-butoxy, sec-butoxy, pentoxy, 3-pentoxy, or hexyloxy.

The term "cycloalkyl" refers to a saturated all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Non-limiting examples of cycloalkyls include cyclopropyl, cyclobutyl, cyclopentyl, and cyclohexyl.

The term "heteroaryl" as used herein refers to a single aromatic ring that has at least one atom other than carbon in the ring, wherein the atom is selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Mu-Opioid Receptor (MOR) Agonist

As used herein the term "mu-opioid receptor (MOR) agonist that is excluded from the central nervous system (CNS)" includes small molecule drugs that are a substrate for a transport protein expressed in the endothelial cells constituting the blood-brain-barrier (BBB); this transport protein is termed p-glycoprotein or P-gp, and its function is to export certain substrates from the BBB into the blood. Morphine, fentanyl, meperidine, methadone and loperamide are all substrates for P-gp, but loperamide's susceptibility to export from the CNS by P-gp is almost ten times that of morphine, fentanyl and meperidine (Dagenais et al., Biochem Pharmacol 67: 269-276, 2004); therefore, the latter three drugs produce significant CNS-mediated effects whereas loperamide does not. Analogs of loperamide with similar properties and clinical application include [8-(3,3-Diphenyl-propyl)-4-oxo-1-phenyl-1,3,8-triaza-triazaspiro [4.5]dec-3-yl]-acetic acid (DiPOA)(Valenzano, K. J. et al., *J Pharmacol Exp Ther*, 310: 783-792, 2004; Whiteside, G. T. et al., J Pharmacol Exp Ther 310: 793-799), or diphenoxylate and its metabolite diphenoxin.

In one embodiment, the mu-opioid receptor (MOR) agonist that is excluded from the CNS is 5 times more susceptible to be exported the CNS by P-gp than morphine.

In one embodiment, the mu-opioid receptor (MOR) agonist that is excluded from the CNS is 8 times more susceptible to be exported the CNS by P-gp than morphine.

In one embodiment, the mu-opioid receptor (MOR) agonist that is excluded from the CNS is 10 times more susceptible to be exported the CNS by P-gp than morphine.

In one embodiment, the mu-opioid receptor (MOR) agonist that is excluded from the CNS is 20 times more susceptible to be exported the CNS by P-gp than morphine.

In one embodiment, the mu-opioid receptor (MOR) agonist that is excluded from the CNS is selected from the group consisting of loperamide, diphenoxylate and diphenoxin; and pharmaceutically acceptable salts thereof.

In one embodiment, the mu-opioid receptor (MOR) agonist that is excluded from the CNS is loperamide, or a pharmaceutically acceptable salt thereof.

In one embodiment, the mu-opioid receptor (MOR) agonist that is excluded from the CNS is selected from the mu-opioid receptor (MOR) agonists as described in United States Patent Application Publication Number US 2004/0152689 (U.S. Pat. No. 7,202,259).

In one embodiment, the mu-opioid receptor (MOR) agonist that is excluded from the CNS is a compound of formula I

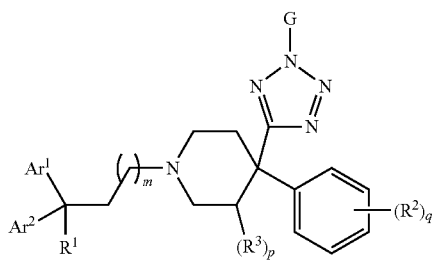

wherein:
$Ar^1$ is $C_{3-8}$ cycloalkyl, phenyl, naphthyl, anthryl, phenanthryl or 5 to 7 membered heteroaryl, each being unsubstituted or substituted with one or more $R^2$ groups;
$Ar^2$ is phenyl, naphthyl, anthryl, phenanthryl or 5 to 7 membered heteroaryl, each being unsubstituted or substituted with one or more $R^2$ groups;
G is —H, -L-$(CH_2)_n CO_2 R^4$, -L-$(CH_2)$—$R^5$, —$(C_{1-5}$ alkylene$)CO_2 R^4$, or —$(C_{1-5}$ alkylene$)R^5$;
L is —C(O)—, —SO$_2$—, or —SO—;
$R^1$ is H, —C(O)NH$_2$, —C(O)NHOH, —CO$_2 R^4$, —CHO, —CN, $C_{1-4}$ alkyl, —C(O)NH($C_{1-4}$ alkyl), or —C(O)N($C_{1-4}$ alkyl)$_2$;
$R^2$ and $R^3$ are each independently halo, $C_{1-3}$ alkyl, —O($C_{1-3}$ alkyl), —NH($C_{1-3}$ alkyl), or —N($C_{1-3}$alkyl)$_2$;
$R^4$ is —H, $C_{1-10}$ alkyl, —CH$_2$O($C_{1-4}$alkyl), —CH$_2$N($C_{1-4}$alkyl)$_2$, or —CH$_2$NH($C_{1-4}$ alkyl);
$R^5$ is —NH$_2$, —NHSO$_2 R^4$, —C(O)NH$_2$, —C(O)NHOH, —SO$_2$NH$_2$, —C(O)NH($C_{1-4}$ alkyl), —C(O)N($C_{1-4}$ alkyl)$_2$, —SO$_2$NH($C_{1-4}$ alkyl), —SO$_2$N($C_{1-4}$ alkyl)$_2$, —H, —OH, —CN, $C_{3-8}$ cycloalkyl, phenyl, naphthyl, anthryl, phenanthryl or 5 to 7 membered heteroaryl, each being unsubstituted or substituted with one or more $R^2$ groups;
m is an integer ranging from 0 to 4;
n is an integer ranging from 1 to 4;
p is 0 or 1; and
q is an integer ranging from 0 to 3;
or a pharmaceutically acceptable salt thereof.

In one embodiment, the mu-opioid receptor (MOR) agonist that is excluded from the CNS is 4-[4-(2-carbamoylm-ethyl-2H-tetrazol-5-yl)-4-phenyl-piperidin-1-yl]-N,N-dimethyl-2,2-diphenylbutyramide, or a pharmaceutically acceptable salt thereof.

In one embodiment, the mu-opioid receptor (MOR) agonist that is excluded from the CNS is not 4-[4-(2-carbamoylmethyl-2H-tetrazol-5-yl)-4-phenyl-piperidin-1-yl]-N,N-dimethyl-2,2-diphenylbutyramide, or a pharmaceutically acceptable salt thereof.

Delta-Opioid Receptor (DOR) Agonist

In one embodiment, the delta-opioid receptor (DOR) agonist is selected from the group consisting of: oxymorphindole, N-benzyloxymorphindole, N,N-diethyl-4-(phenyl-piperidin-4-ylidenemethyl)-benzamide (ARM390), 9-(8-azabicyclo[3.2.1]oct-3-ylidene)-9H-xanthene-3-carboxylic acid diethylamide (JNJ20788560), TRV250, amoxapine, N-cyclopropylmethyl-[7α,8α,2',3']-cyclohexano-1'[S]-hydroxy-6,14-endo-ethenotetrahydronororipavine (BU-48), 4-[(R)-[(2S,5R)-2,5-dimethyl-4-prop-2-enylpiperazin-1-yl]-(3-hydroxyphenyl)methyl]-N,N-diethylbenzamide (BW373U86), trans-4-(p-Bromophenyl)-4-(dimethylamino)-1-(2-(thiophen-2-yl)ethyl)cyclohexanol (C-8813), cebranopadol, cyclorphan, Tyr-D-Ala-Gly-Phe-D-Leu-OH (DADLE), deltorphin II, desmethylclozapine, 4-((αS)-α-((2S,5R)-2,5-dimethyl-4-(3-fluorobenzyl)-1-piperazinyl)benzyl)-N,N-diethylbenzamide (DPI-221), 4-[(R)-[(2S,5R)-2,5-dimethyl-4-benzylpiperazin-1-yl]-(3-hydroxyphenyl)methyl]-N,N-diethylbenzamide (DPI-287), 3-[(R)-[(2S,5R)-2,5-dimethyl-4-prop-2-enylpiperazin-1-yl]-(3-hydroxyphenyl)methyl]-N-(3-fluorophenyl)-N-methylbenzamide (DPI-3290), hemorphin-4, katamine, Leu-enkephalin, Met-enkephalin, mitragynine, norbuprenorphine, N-phenethyl-14-ethoxymetopon, N,N-diethyl-4-((8-phenethyl-8-azabicyclo[3.2.1]oct-3-ylidene) phenylmethyl)benzamide (RWJ-394674), samidorphan, 4-[(R)-[(2S,5R)-4-allyl-2,5-dimethylpiperazin-1-yl](3-methoxyphenyl)methyl]-N,N-diethylbenzamide (SNC-80), 7-spiroindanyloxymorphone, 3-[(4aS,12aR)-2-Methyl-1,3,4,5,12,12a-hexahydropyrido[3,4-b]acridin-4a(2H)-yl]phenol (TAN-67), tianeptine, and xorphanol; and pharmaceutically acceptable salts thereof.

In one embodiment, the delta-opioid receptor (DOR) agonist is oxymorphindole, N-benzyloxymorphindole, N,N-diethyl-4-(phenyl-piperidin-4-ylidenemethyl)-benzamide (ARM390), 9-(8-azabicyclo[3.2.1]oct-3-ylidene)-9H-xanthene-3-carboxylic acid diethylamide (JNJ20788560), or TRV250, or a pharmaceutically acceptable salt thereof.

In one embodiment, the delta-opioid receptor (DOR) agonist is oxymorphindole or N-benzyloxymorphindole, or a pharmaceutically acceptable salt thereof.

In one embodiment, the delta-opioid receptor (DOR) agonist is oxymorphindole, or a pharmaceutically acceptable salt thereof.

In one embodiment, the delta-opioid receptor (DOR) agonist is N-benzyloxymorphindole, or a pharmaceutically acceptable salt thereof.

In one embodiment, the delta-opioid receptor (DOR) agonist is N,N-diethyl-4-(phenyl-piperidin-4-ylidenemethyl)-benzamide (ARM390), or a pharmaceutically acceptable salt thereof.

In one embodiment, the delta-opioid receptor (DOR) agonist is 9-(8-azabicyclo[3.2.1]oct-3-ylidene)-9H-xanthene-3-carboxylic acid diethylamide (JNJ20788560), or a pharmaceutically acceptable salt thereof.

In one embodiment, the delta-opioid receptor (DOR) agonist is selected from the delta-opioid receptor (DOR)

agonists as described in United States Patent Application Publication Number US 2012/0245181 (U.S. Pat. No. 8,835, 488).

In one embodiment, the delta-opioid receptor (DOR) agonist is a compound of formula II:

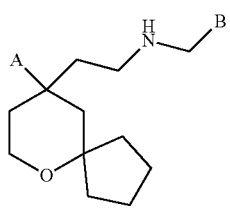

II wherein:

A is heteroaryl that is optionally substituted with halo, hydroxyl, $C_{1-6}$ alkyl, $C_{1-6}$ haloalkyl, $C_{1-6}$ alkoxy, nitro, or cyano; and B is heteroaryl that is optionally substituted with halo, hydroxyl, $C_{1-6}$ alkyl, $C_{1-6}$ haloalkyl, $C_{1-6}$ alkoxy, nitro, or cyano;

or a pharmaceutically acceptable salt thereof.

In one embodiment, A is an optionally substituted pyridyl, and B is an optionally substituted pyridyl.

In one embodiment, the delta-opioid receptor (DOR) agonist is:

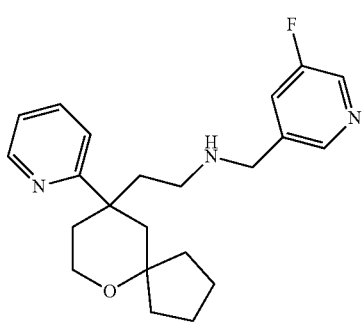 [SMILES: Fc1cncc(CNCCC2(c3ccccn3)CCOC3(CCCC3)C2)c1]

or a pharmaceutically acceptable salt thereof

Compositions and Methods

In certain embodiments, the invention provides a composition comprising 1) a mu-opioid receptor (MOR) agonist that is excluded from the CNS, 2) oxymorphindole or N-benzyloxymorphindole, or a pharmaceutically acceptable salt thereof, and 3) a pharmaceutically acceptable carrier.

In certain embodiments, the invention provides a composition comprising 1) 4-[4-(2-carbamoylmethyl-2H-tetrazol-5-yl)-4-phenyl-piperidin-1-yl]-N,N-dimethyl-2,2-diphenyl-butyramide, or a pharmaceutically acceptable salt thereof, 2) a delta-opioid receptor (DOR) agonist, and 3) a pharmaceutically acceptable carrier.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

In one embodiment, the composition of the invention is adapted for oral administration.

In one embodiment, the composition of the invention is adapted for topical administration via a transdermal patch.

In one embodiment, the composition of the invention is adapted for topical administration to a site of inflammation or injury.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compounds may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. In one embodiment the compositions are formulated for topical administration. In one embodiment, the carrier for topical administration is 50% ethanol in water. In one embodiment the compositions are formulated for administration via transdermal patch. In one embodiment the invention provides a transdermal patch comprising a composition of the invention. In one embodiment the compositions are formulated for local topical administration (i.e. on an arthritic hand). In another embodiment the compositions are formulated for topical ophthalmic administration (e.g. for intraoperative use during ophthalmic surgery).

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In one embodiment, the term "animal" as used herein refers to humans, higher non-human primates, rodents, or domestic animals: cows, horses, pigs, sheep, dogs and cats. In one embodiment, the animal is a human. The term "patient" as used herein refers to any animal including mammals. In one embodiment, the patient is a mammalian patient. In one embodiment, the patient is a human patient.

The invention will now be illustrated by the following non-limiting Examples.

EXAMPLES

Example 1 Preparation of (4bS,8aS,14bR)-14-benzyl-7-methyl-5,6,7,8,8a,9,14,14b-octahydro-4,8-methanobenzofuro[2,3-a]pyrido[4,3-b]carbazole-1,8a-diol (6)

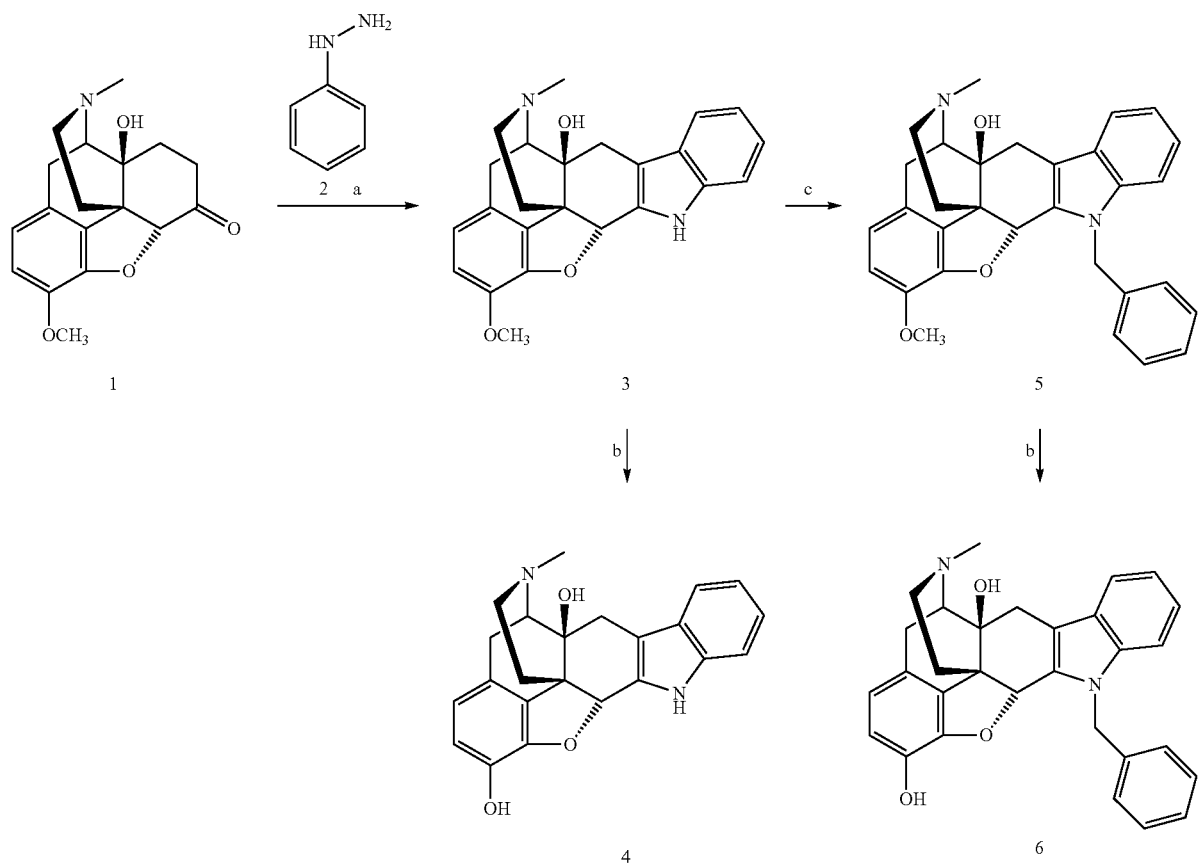

a) Acetic acid, r.t.-90° C., HCl, then NH$_4$OH; b) methylene chloride, -78° C. to +10° C., BBr$_3$, then NH$_4$OH;
c) methylene chloride, Benzyl bromide, Tetrabutylammonium hydrogen sulfate.

BOMI 6 was obtained by alkylation of indole nitrogen of OMI. Methyl OMI (3) was synthesized by condensation of oxycodone (1) with phenyl hydrazine (2) in acetic acid. The reaction was monitored with a thermometer; as soon as the inner temperature reached 90° C., an excess of HCl in dioxane (4M) was added, and the reaction continued for another 10 minutes. Methyl OMI (3) was precipitated as a solid HCl salt and was filtered; subsequent quenching with ammonium hydroxide solution afforded the parent compound free base, which was converted to OMI (4) in methylene chloride by BBr$_3$ (Iijima, I., et al., *J. Med. Chem.* 1978, 21, 398-400) (7 equivalents) under cooling with acetone/CO$_2$, finally quenching with ammonium hydroxide at 10° C. completed the synthesis. OMI is also conveniently obtainable by condensation of oxymorphone with phenylhydrazine in acetic acid at 90° C.; subsequent addition of excess HCl in dioxane (4M) at the same temperature gives OMI as the HCl salt in a quantitative yield. Methoxy OMI 3 was alkylated with benzyl bromide under a phase transfer condition using a catalytic amount of tetrabutylammonium hydrogen sulfate (TBAHS; see Ho, T.-L., et al., *Tetrabutylammonium hydrogen sulfate.* John Wiley & Sons, Inc.: 2006) and NaOH (50%) in methylene chloride. The intermediate product 5 was obtained with 82% yield. Finally, the intermediate indole 5 was deprotected with BBr$_3$ and afforded the target indole 6.

Column chromatography was performed with silica gel (E. Merck 60, 230-400 mesh). The R$_f$ value reported for TLC analysis was determined on precoated (0.25 mm) silica gel 60E-254 fluorescent UV 254 plates purchased from E. Merck using the indicated solvent system. Melting points (mp) were determined on a Mel-Temp apparatus in open capillaries and are uncorrected. Analytical HPLC was performed on a Shimadzu LC-8A [BDS Hypersil C-18, serial number: 28105-254030; diameter: 4.6×250 mm] and compounds were eluted with methanol/0.01M (NH$_4$)$_2$HPO$_4$ (95:5) at a flow rate of 0.5 ml/min. Electron impact spectra (EI-MS) were obtained with a Finnegan MAT 95 mass spectrometer. $^1$H and $^{13}$C NMR spectra were obtained on a Varian mercury-300 instrument. Chemical shifts are reported in ppm (δ) relative to internal Me$_4$Si in CDCl$_3$ or d$_6$-DMSO.

a. Synthesis of (4bS,8aS,14bR)-1-methoxy-7-methyl-5,6,7,8,8a,9,14,14b-octahydro-4,8-methano-benzofuro[2,3-a]pyrido[4,3-b]carbazol-8a-ol (3)

Oxycodone (2 g, 6.34 mmol) was dissolved in 10 mL acetic acid and 0.8 mL phenyl hydrazine added. The mixture was warmed up to 90° C. At this temperature 5 mL HCl (4N in 1,4-dioxane) was added. The precipitate, which occurred after 10 min., was filtered via sintered glass and washed with ethyl acetate. The HCl salt of 3 was dissolved in methylene chloride and quenched with ammonium hydroxide. The slightly yellow material is obtained quantitatively. $^1$H-NMR ($d_6$-DMSO): 12 (s, br, 1H), 11.3 (s, 1H), 9.3 (s, 1H), 7.4-6.9 (m, 4H), 6.7-6.4 (AB, $J_{AB}$=8.22 Hz, 2H), 5.7 (s, H-5), 3.45 (s, 3H), 3.8-1.85 (m, unresolved). MS(ESI): M=388.46, calculated. For $C_{24}H_{24}N_2O_3$, found, (M+1)$^+$=389.2.

b. (4bS,8aS,14bR)-14-benzyl-1-methoxy-7-methyl-5,6,7,8,8a,9,14,14b-octahydro-4,8-methanobenzo-furo[2,3-a]pyrido[4,3-b]carbazol-8a-ol (5)

Methyl OMI (3) (1 g, 2.57 mmol) was dissolved in methylene chloride and one equivalent benzyl bromide added. After addition of catalyst tetrabutylammonium hydrogen sulfate, the mixture was treated with a NaOH (50%, 10 mL) and stirred overnight at room temperature. The next day, the mixture was quenched with water and the organic layer separated, water layer re-extracted twice with 25 mL methylene chloride. The combined extracts were dried over anhydrous sodium sulfate to provide compound (5).

c. (4bS,8aS,14bR)-14-benzyl-7-methyl-5,6,7,8,8a,9,14,14b-octahydro-4,8-methanobenzofuro[2,3-a]pyrido[4,3-b]carbazole-1,8a-diol (6)

After evaporation of the solvent from the product of step b above, the residue was dissolved in anhydrous methylene chloride, cooled with dry ice/acetone and 7 equivalents BBr$_3$ (1M, methylene chloride) were added. The entire mixture was stirred until the cooling bath warmed up to 10° C. At this temperature, this mixture was treated with ammonium hydroxide until pH 10. The organic layer was separated, water layer re-extracted (2×25 mL, methylene chloride), and the combined extracts were dried over sodium sulfate. After evaporation of solvent, colorless solid materials were isolated. In general the products are clean, but a short path of silica column with a solvent combination of CH$_2$Cl$_2$/MeOH/NH$_4$OH (95:4.5:05) was used for purification. Yield of (6): 60% from (5); $^1$H-NMR ($d_6$-DMSO): 4-6.9 (m, 9H), 6.5 (m, 2H), 5.7 (s, H-5), 5.46 (s, 2H), 3.45-1.7 (m, unresolved), 2.41 (s, 3H). m.p.=>250 dec.; 464.2100. calculated for $C_{30}H_{28}N_2O_3$, found, (M+1)$^+$=465.2115+). Purity of the final product (6) was over 98% based on analysis on HPLC column [BDS Hypersil C-18, serial number: 28105-254030; diameter: 4.6×250 mm]; the compound was eluted with methanol/0.01M (NH$_4$)$_2$HPO$_4$ (95:5) at a flow rate of 0.5 mL/min. The final product was acidified with HCl.

Example 2 Evaluation of Analgesic Activity of Compounds 4 and 6

Opioid analgesics are the choice of drugs in the treatment of acute and chronic pain; they elicit their effect through opioid receptors. Opioid receptors are classified as MOR (mu), DOR (delta), and KOR (kappa) with a fourth non-classical opioid receptor NOR (nociceptin/orphinan) (Dhawan, B. N. et al., Pharmacol. Rev. 1996, 48, 567-592). Morphine, one of the main opioid analgesics for chronic pain treatment, exerts its analgesic effect mainly by binding to MOR, but repeated use of morphine produces a host of unwanted side effects, including tolerance and dependence (Benyamin, R. et al., Pain Physician 2008, 11, S105-20). Mice in which the MOR gene was deleted did not display morphine-induced analgesia (Kieffer, B. L. et al., Trends Pharmacol. Sci. 1999, 20, 19-26). MORs are not isolated entities in vivo, but interact with other receptors (Negus, S. S. et al., Eur. J. Pharmacol. 2009, 602, 92-100). These interactions modulate MOR. Modulation of MOR by DOR is intensively studied in vitro as well as in vivo. In vivo studies, for example, simultaneous blocking of DOR while activating MOR results in enhanced morphine analgesia and reduced tolerance and dependence (Kabli, N. et al., Br. J. Pharmacol. 2010, 161, 1122-1136; He, S.-Q. et al., Neuron 69, 120-131; Abdelhamid, E. E., et al., J. Pharmacol. Exp. Ther. 1991, 258, 299-303; and Dietis, N., et al., Br. J. Anaesth. 2009, 103, 38-49). In some studies it was also suggested that a small amount of a DOR agonist can potentiate the binding and signaling of MOR agonists without serious side effects (Lee, Y. S., et al., J. Med. Chem. 2011, 54, 382-386); in vivo experiments quantifying the antinociceptive efficacy of morphine combined with the peptide agonist deltorphin II were consistent with this observation (Schramm and Honda, Pain 2010, 151, 763-770). Other in vivo studies characterized co-administration of the MOR agonist morphine with the DOR antagonist naltrindole (NTI) and a bivalent ligand that combined a MOR agonist pharmacophore with a DOR antagonist pharmacophore with a tether. Both the co-administration and bivalent ligand approaches suffer from a variety of drawbacks such as pharmacokinetics, formulations etc. In comparison to classical analgesics, however, biofunctional analgesic drugs represent alternative new medications which may have favorable side-effect profiles in human (Ananthan, S., et al., The AAPS Journal, 2006, 8, E118-E125; Lee, Y. S., et al., J. Med. Chem., 2011, 54, 382-386). The compound BOMI (6) has the potential to be the bifunctional drug that might be an analgesic devoid of liabilities associated with the classical opioid drugs. BOMI is a synthetic opioid derived from the MOR agonist oxymorphone and also contains the indole address portion of the DOR antagonist NTI.

Opioids used in clinical practice exert their effects through MOR. However, their potency, efficacy, and side effects vary among patients (Pasternak, G. W, Clin. J. Pain 26 Suppl 10, S3-9, 2010). The differences indicate the involvement of other receptors in the analgesic effects of these drugs. In the last decade, an explosion of publications has addressed the modulation of MOR by other receptors. The main modulator of MOR regarding opioid side effects such as tolerance and dependence is DOR, and MOR-DOR heteromer formation in cultured cells results in pharmacological and functional properties distinct from those of the corresponding homomeric protomers.

In a recent report, Gomes et al. investigated MOR-DOR heteromers in cultured cells and found that binding of one agonist to one protomer promotes the binding and signaling of the second agonist to the second protomer (Gomes, I. et al., Mol. Pharmacol. 79, 1044-1052). A similar allosteric modulation was also observed in vivo. For example, an ultra small dose of the DOR antagonist NTI not only augmented the analgesic effects of spinally administered morphine in rats, it also inhibited the development of tolerance to morphine (Dietis, N. et al., Br. J. Anaesth. 2009, 103, 38-49). Agonist at the DOR modulates also the antinociceptive efficacy of MOR agonists such as morphine; this modulation can be positive as well as negative (Vaught, J. L. et al., *J. Pharmacol. Exp. Ther.* 1979, 208, 86-90; Porreca, F. et al., *J. Pharmacol. Exp. Ther.* 1992, 263, 147-152; and Qi, J. N. et al., *J. Pharmacol. Exp. Ther.* 1990, 254, 683-689). The in vivo relevance of MOR-DOR heteromers has further advanced via generation of antibodies selectively recognizing these heteromers in brain, in particular in pain processing areas of CNS (Gupta, A. et al., Sci. *Signal.* 2010, 3, 1-7). Keeping the above information in mind, an in vitro calcium mobilization experiment was carried out with NTI followed by OMI. The antagonist NTI was devoid of any calcium mobilization while the partial agonist OMI showed selective mobilization in the MOR-DOR co-expressing cell line. Studies with BOMI were mixed, stimulation of MOR most active.

OMI (Portoghese, P. S., et al., *J. Med. Chem.* 1990, 33, 1714-20) and BOMI were tested in vivo. Tolerance studies in mice showed that interthecally administered OMI and (6) did not produce tolerance. OMI and its derivative (6) were tested in naloxone-precipitated dependence studies and neither OMI nor (6) produced dependence. Oral gavage of OMI and (6) produced the peak antinociceptive effect at 30 minutes; further they were taken in vivo studies in mice and challenged by antagonists such as NTI, norBNI and β-FNA. The results are depicted in FIGS. 1a-1d. OMI and (6) were antagonized by β-FNA when administered intrathecally as well as intracerebroventriclarly; antagonism of (6) by β-FNA was more significant, suggesting that β-FNA is a MOR-DOR heteromer-selective antagonist. Therefore, it was concluded that OMI and (6) both are MOR-DOR heteromer-selective agonists.

Figure 2A:
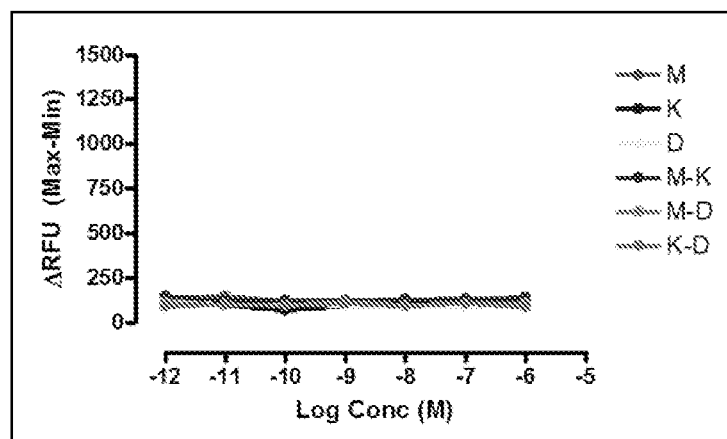
FIGS. 2a-2c show calcium mobilization studies for Example 3.
Figure 2B:
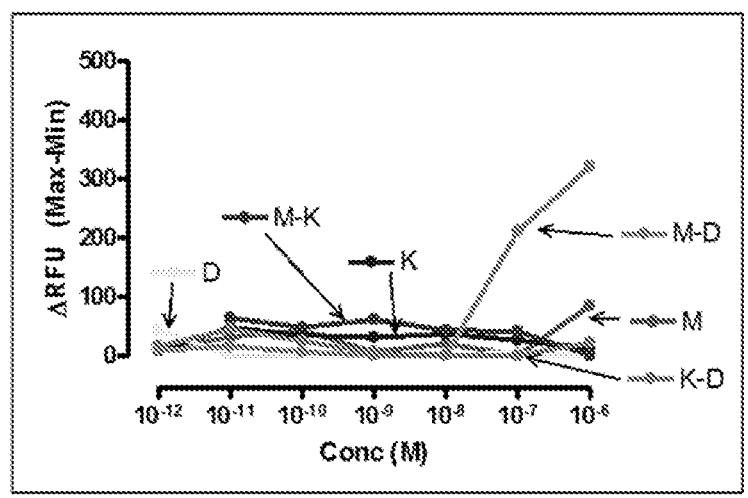
Figure 2C:
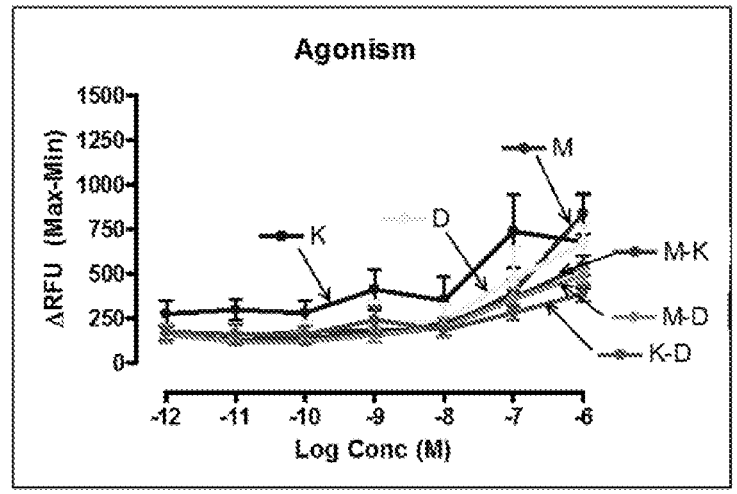

Example 3 In Vitro Studies of Compounds 4 and 6—Intracellular $Ca^{2+}$ Release Studies The target compounds were tested for agonist activity using an intracellular calcium release assay. Briefly, HEK-293 cells were transfected with a chimeric $\Delta 6\text{-}G_{qi4\text{-}myr}$ protein employed to measure intracellular $Ca^{+2}$ ion release upon receptor activation. Cells stably expressing the chimeric protein were selected from transiently transfected cells in zeocin-containing medium (DMEM+10% fetal bovine serum+1% penicillin/streptomycin+0.1 µg/mL zeocin). Opioid receptors were transiently transfected using different combinations of DNA for heteromers (mu-delta, mu-kappa, kappa-delta) or for singly expressing homomers (mu, delta, kappa). Intracellular calcium release was measured using a FLIPR calcium kit (Molecular Devices) in a FlexStation3 apparatus. For each compound, concentration-response profiles were established by measuring the fluorescence for 90 seconds after addition of the compound and determining the peak effect (maximum-minimum). A concentration-response curve was plotted for the change in Relative Fluorescence Units (ΔRFU) vs. concentration. The calcium mobilization of the antagonist NTI and partial agonist OMI were studied. NTI did not show calcium mobilization in any cell line tested; in comparison, the partial agonist 4 demonstrated a profile of MOR-DOR heteromer selectivity. Compound (6), which has a tolerance- and dependence-free profile in in vivo studies (i.t. injection and oral gavage), manifests a calcium mobilization profile indicating that is predominantly MOR-DOR heteromer-selective. Data are shown in FIG. 2a-c.

Example 4 In Vivo Studies of Compounds 4 and 6—Assessment of Potency

Figure 3:
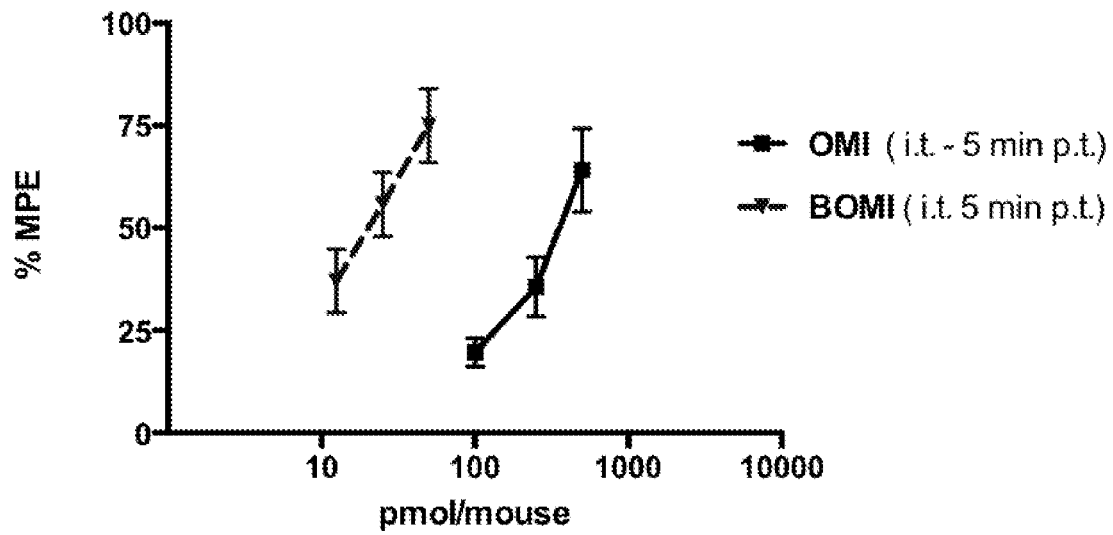
FIG. 3 shows potency data of OMI and BOMI when administered intrathecally from Example 4.
Figure 4:
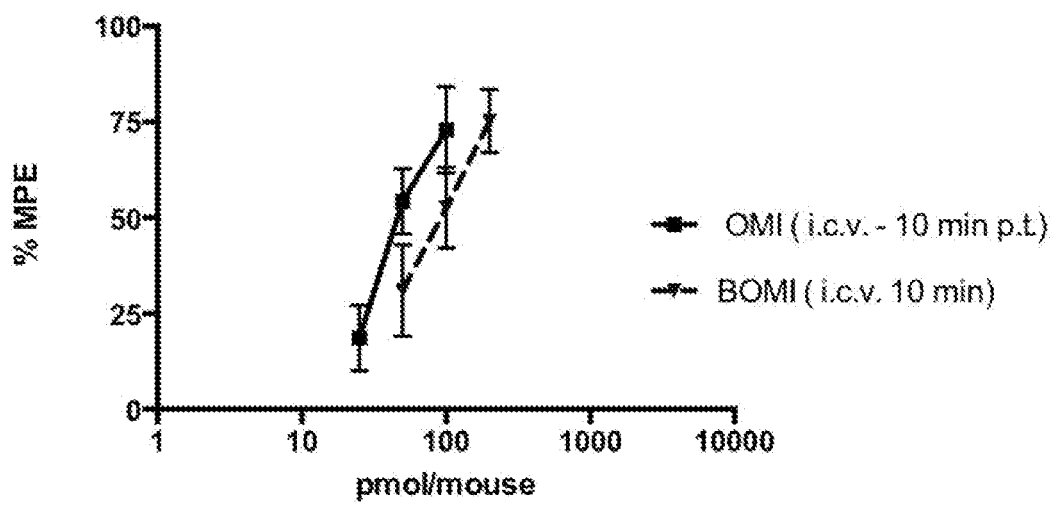
FIG. 4 shows potency data of OMI and BOMI when administered intrathecally from Example 4.

OMI (4) or BOMI (6) were administered via either i.t. or i.c.v. routes and percent maximum possible antinociception (% MPE) determined at 5 or 10 min post-treatment, respectively. FIG. 3 shows the i.t. data demonstrating that BOMI (6) is 20 times more potent than the parent compound OMI (4). FIG. 4 shows the i.c.v. data demonstrating that BOMI (6) is three times more potent than the parent compound OMI (4).

Example 5 In Vivo Studies of Compounds 4 and 6—Assessment of Tolerance

Eighty percent effective doses of OMI (4) or BOMI (6) were administered either i.c.v. or i.t. once on day 1 and again on day 2 and the % MPE determined on both days. Tolerance, which is evidenced by reduced % MPE on day 2, was evident (~30-50% MPE) for both agents after i.c.v. administration; neither agent injected i.t. produced antinociceptive tolerance (data not shown).

Example 6 In Vivo Studies of Compounds 4 and 6—Assessment of Dependence

Morphine, OMI and BOMI were tested for dependence using the naloxone withdrawal jumping protocol (Marshall, I. et al., *Br. J. Pharmacol.* 1969, 37, 505P-506P; and El-kadi, A. O. et al., *General Pharmacology: The Vascular System* 1994, 25, 1505-1510). On day one the $ED_{80}$ dose was injected 3 times per day 4 hours apart using the s.c. route of administration. On day 2 two times $ED_{80}$ and day 3 and 4 with four times the $ED_{80}$ were injected at the same times used on day one. On the fifth day each animal received a bolus of the top dose followed three hours later by a single dose of naloxone s.c. (10 or 50 mg/kg) and placed in individual circular Plexiglas observation chambers (6.5"× 9"). The number of jumps was observed for 10 minutes. At 10 mg/kg and 50 mg/kg naloxone precipitated withdrawal in the morphine-treated animals with a mean 91.5 jumps and 99.3 jumps, respectively. The average number of jumps for both OMI and BOMI after both doses of naloxone was 1 jump. These two compounds did not create any dependence that was measured in this study.

Example 7 Oral Gavage in Mice of Compounds 4 and 6

OMI and BOMI were further evaluated using oral gavage in mice; the data are summarized in Table 1. Animals are restrained by the scruff and held upright (vertically) to maintain a straight line from the mouth to the esophagus. Prior to dosing, the distance from the oral cavity to the caudal point of the sternum is gauged with the gavage needle. Using a bulb-tipped gastric gavage needle attached to a 1 mL syringe, the needle is passed along the roof of the animal's mouth and into the esophagus, stopping at the pre-measured distance. The drug is slowly injected and the needle removed. Drugs are administered in a volume of 10 mL/kg.

TABLE 1

Summary of oral gavage of OMI and BOMI

| Compound (oral, 5 mg/kg) | % MPE Time (min.) | | | |
|---|---|---|---|---|
| | 20 | 30 | 60 | 120 |
| OMI (4) | 38.0 ± 8.4 | 29.5 ± 4.5 | 38.5 ± 10.7 | |
| BOMI (6) | 38.3 ± 10.4 | 19.6 ± 4.8 | 42.8 ± 6.2 | 38.4 ± 8.4 |

Example 8 Efficacy Testing

Animals:

Adult male I.C.R. mice (25-35 g) were housed four to a cage and maintained on a 12 h light/dark cycle, with ad libitum access to food and water. Testing was performed during the light phase. The University of Minnesota Institutional Animal Care and Use Committee approved all protocols employing animals.

Drug Preparation & Administration:

The compounds used were: loperamide HCl (Sigma, St. Louis, Mo.); oxymorphindole HCl (A gift from the laboratory of Phillip Portoghese, University of Minnesota); naltrindole HCl (Tocris, Ellsville, Mo.); naloxone methiodide (Sigma, St. Louis, Mo.); and beta-funaltrexamine (β-FNA, a gift from the laboratory of Phillip Portoghese, University of Minnesota). Stock solutions of loperamide HCl and oxymorphindole HCl were prepared with 20% Cremaphor EL or 5% DMSO+5% Cremaphore EL in 0.9% saline; dilutions to doses administered to animals resulted in final DMSO or Cremaphor concentrations of less than or equal to 1%. All other drugs were solubilized in normal saline. All drugs were diluted to testing concentrations with 0.9% sterile saline. The routes and volumes of administration were: intrathecal (i.t.), intraplantar (i.pl.), 30 μL; subcutaneous (s.c.), 10 μL/g. For i.pl. injections, animals were lightly anesthetized using 2.5% isoflurane and the injections were made in the left hindpaw.

Behavioral Measures:

Thermal nociception was measured either using a warm water tail flick test or using the Hargreaves hindpaw method as described previously (Hargreaves, K. et al., Pain 32: 77-88, 1988). Briefly, animals were placed on a heated glass floor (30° C.) and a small plastic box restricted their movement. After allowing the animals to acclimate to the testing environment for a minimum of 15 minutes, a radiant heat lamp was shone on the left hindpaw until the animal withdrew the paw. Paw withdrawal latencies (PWLs) were measured by an IITC plantar stimulator analgesia meter, and a cutoff time of 20 seconds was used to prevent tissue damage. An average of 3-5 PWLs were taken, with a minimum of 30 seconds between tests.

Freund's Complete Adjuvant (FCA)-Induced Hyperalgesia:

After determining naïve PWLs, animals were lightly anesthetized using 2.5% isoflurane, and FCA was administered by i. pl. injection into the left hindpaw. 3-5 days after injection, a robust, inflammatory hyperalgesia was present, and hyperalgesic PWLs were determined.

Spinal Cord Electrophysiology:

Slices of lumbar spinal cord taken from mice and preserved them in oxygenated (95% $O_2$, 5% $CO_2$) artificial cerebrospinal fluid (aCSF). Slices were placed in the recording chamber, and superfused with aCSF containing 1 μM tetrodotoxin, 100 μM picrotoxin, 100 μM amino-phosphonovaleric acid (AP5) and 5 μM strychnine to isolate glutamatergic, AMPA-mediated miniature excitatory post-synaptic currents (mEPSCs). Substantia gelatinosa neurons were visualized with DIC optics (Olympus BX50WI microscope) and whole-cell patch clamped with a glass patch pipette. An Axopatch 200b amplifier was used to record membrane currents at a holding potential of −65 mV. After establishing the basal frequency of spontaneous mEPSCs (~1 Hz), we drove release of glutamate from Nav1.8-ChR2-expressing nociceptors by shining 470 nm light on the slice (frequencies~10 Hz). Once the light-driven mEPSC frequency is determined, increasing concentrations of agonists or their combinations were superfused on the slice and the frequency of mEPSCs recorded. OMI, Lo or their combination inhibited the driven mEPSC frequency.

Spared Nerve Injury (SNI)-Induced Allodynia

SNI was induced in mice as described previously (DeCosterd I. and Woolf C. J., Pain 87: 149-158, 2000). Briefly, the left sciatic nerve and its three terminal branches were exposed under isoflurane anesthesia. The common peroneal and tibial nerves were ligated with a 5.0 silk suture and sectioned distal to the ligation, removing 2-4 mm of the distal nerve stump.

Paw Incision Model of Post-Surgical Pain

Paw incision surgery was conducted as described previously (Brennan, T. J. et al., Pain 64.3 (1996): 493-502). Briefly, an incision was made in the plantar surface of the left hindpaw and the underlying muscle was damaged. Wounds were closed with dissolving suture and animals were placed back in home cage to recover.

Data Analysis: The ED50, in nanomoles with 95% confidence limits, of all agonists and combinations were calculated using the graded dose-response curve method of Tallarida and Murray (Tallarida, R. J. and Murray, R. B., Manual of pharmacological calculations with computer programs, pp. 26-31, Springer-Verlag, NY, 1987). Dose ratios for drug combinations were estimated based on comparison of ED50 values and dose-response curves and were chosen to approximate equi-effective doses. Isobolographic analyses were performed using the numerical method (Tallarida, Pain 49: 93-97, 1992; Ossipov et al., Anesthesiology 86:1-9 1997). Theoretical additive and observed combination ED50 values were compared statistically via the Student's t test with the JFlashCalc Pharmacological Calculations Program software package generously provided by Dr. Michael Ossipov (Department of Pharmacology, University of Arizona College of Medicine, Tucson, Ariz.). For all isobolograms, error bars for theoretical additive and observed combination ED50 values represent the vector sum of vertical and horizontal confidence limits.

Results

Figure 5A:
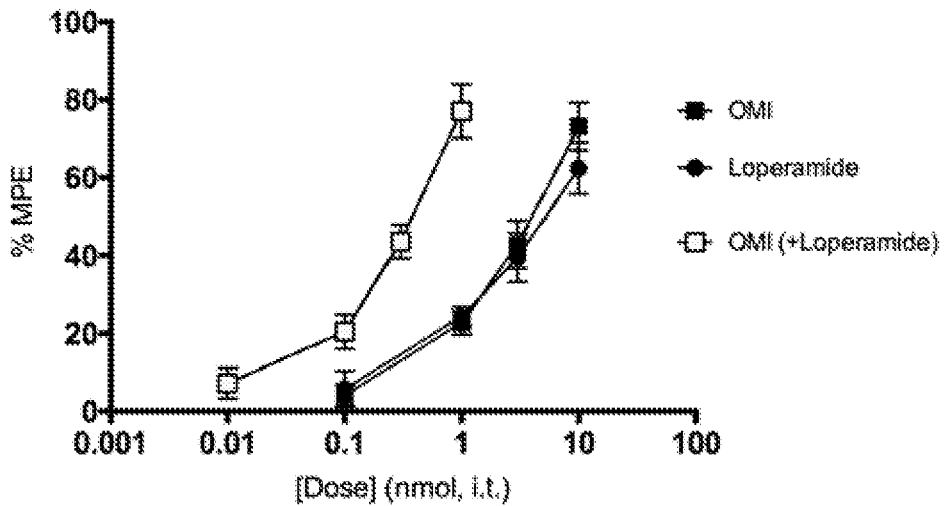
FIGS. 5a and 5b show analgesic properties of loperamide, OMI or combination in naïve animals.
Figure 5B:
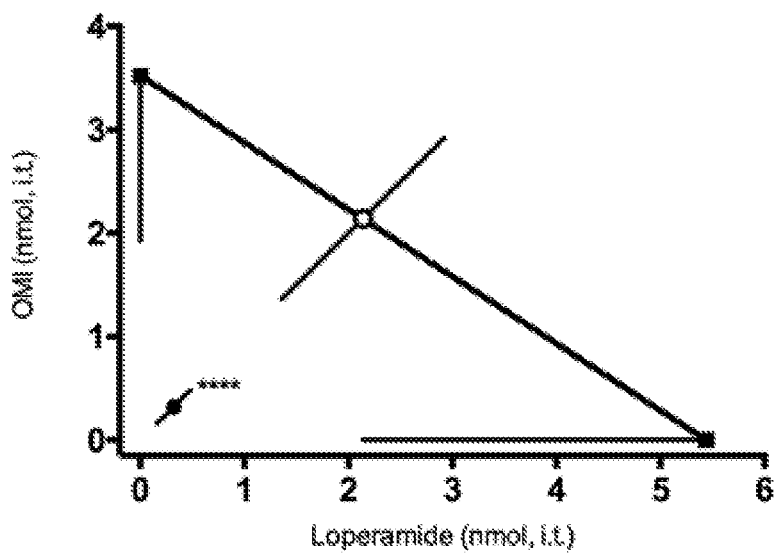

Different agonists were reported to show differential effects when given in combination in a recent publication (Schuster D. J. et al, BJP 172.2(2015):643-653). FIG. 5a shows cumulative dose-response curves in naïve mice following an intrathecal injection. Both loperamide and oxymorphindole (0.1-10 nmol), as well as a 1:1 combination (0.01-1 nmol), produced analgesia in the hot water tail flick assay. The ED50s of the individual drugs were 5.44 nmol (Lo) and 3.52 nmol (OMI), and the ED50 of the combination was 0.64 nmol (n=6 per group). This measured ED50 for the combination was statistically different from the expected additive ED50 ($p<0.0001$), meaning loperamide and oxymorphindole synergize when delivered spinally. This interaction is represented graphically by an isobologram in FIG. 5b. (In the figure legends, * signifies $p<0.05$,  $p<0.01$, * $p<0.001$, **** $p<0.0001$.)

Figure 6:
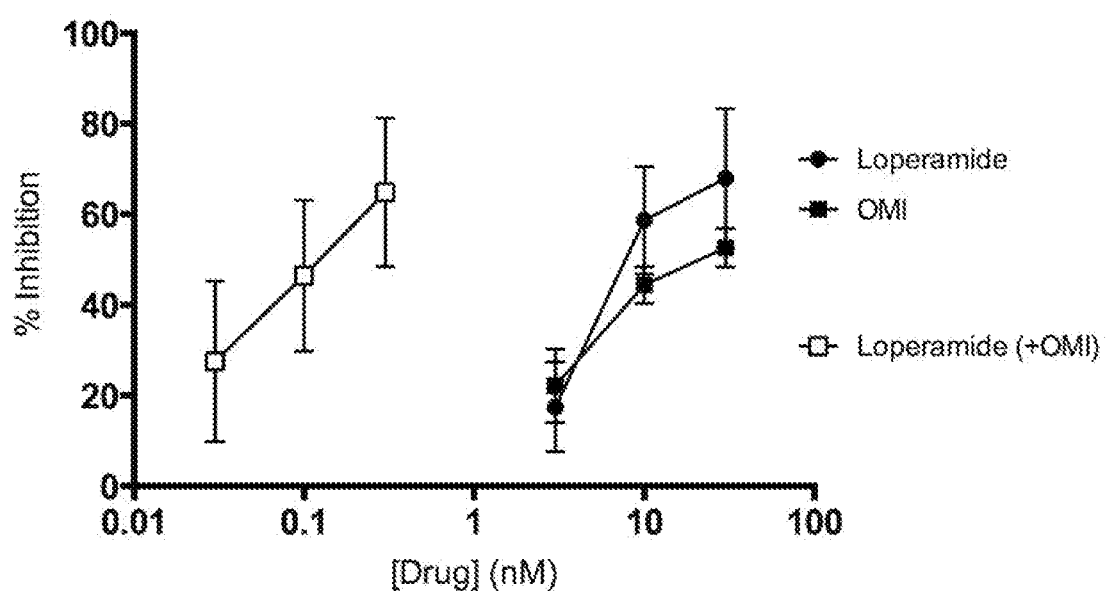
FIG. 6 shows loperamide, OMI, or combination-mediated inhibition of 470 nm light-evoked mEPSCs. mEPSCs were driven using a 470 nm LED shone directly on the dorsal horn of spinal cord slices taken from Nav1.8-ChR2 mice. mEPSC frequency was measured for baseline, blue light, and increasing concentrations of drug or combination. Data are expressed here as a percent inhibition of the light-driven mEPSC frequency.

Having demonstrated that loperamide and oxymorphindole are able to synergize in the spinal cord behaviorally, we tested the hypothesis that this interaction was mediated by primary afferent nociceptive fibers innervating the dorsal horn. Whole cell patch clamp recordings were conducted in spinal cord neurons located in the superficial laminae of the lumbar dorsal horn. For these recordings spinal cord slices were taken from a transgenic mouse line bred to express channelrhodopsin-2 (ChR2), a light-activated cation channel, under the control of the promoter for the voltage-gated sodium channel Nav 1.8. Nav 1.8 is primarily expressed by nociceptive afferents, and ~80% of light-responsive fibers in this mouse line were shown to be polymodal C fibers (Uhelski, M. et al., *J Neurophysiol*, in press, 2017). Therefore, the frequency of mEPSCs driven by 470 nm light was used as a measure of presynaptic nociceptive afferent activity in this assay. FIG. 6 shows the concentration-response curves for loperamide, oxymorphindole or their 1:1 combination to inhibit the mEPSC frequency driven by blue light (n=3-6 cells). Both loperamide and oxymorphindole inhibited mEPSC frequency in a concentration-dependent manner, while the combination was 100-fold more potent. These data mean that loperamide and oxymorphindole bind their respective receptors on the presynaptic terminals of primary afferent nociceptors and inhibit the release of glutamate from these central terminals. By the same token, the combination's shift in potency means that the synergy between loperamide and oxymorphindole is also mediated at these central terminals.

Figure 7A:
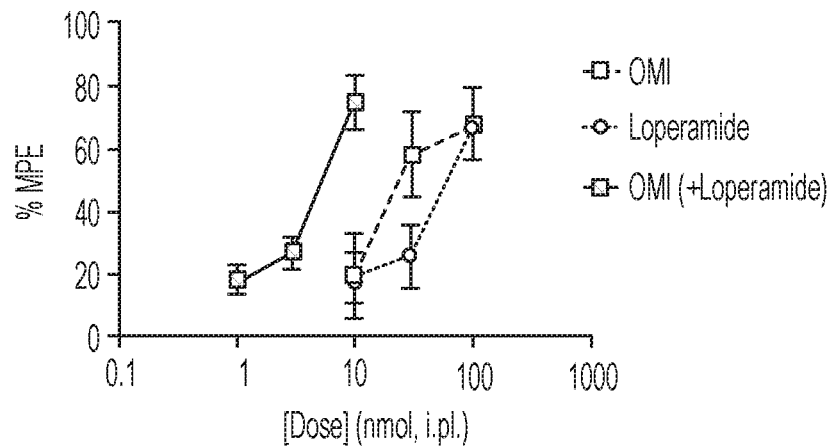
FIGS. 7a-7d show that peripherally administered OMI-Lo synergizes in naive and inflamed animals.
Figure 7B:
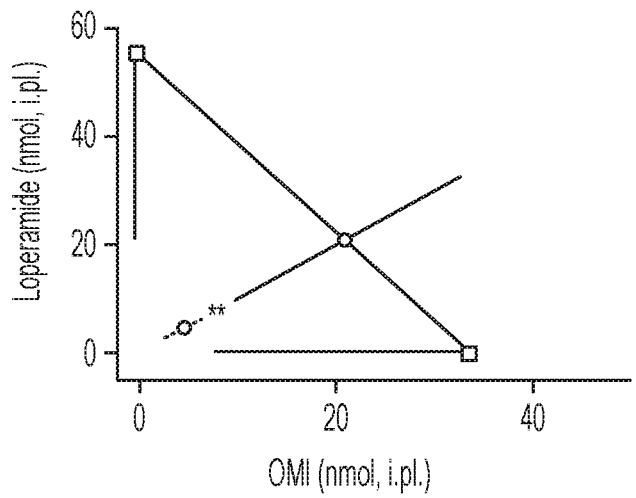
Figure 7C:
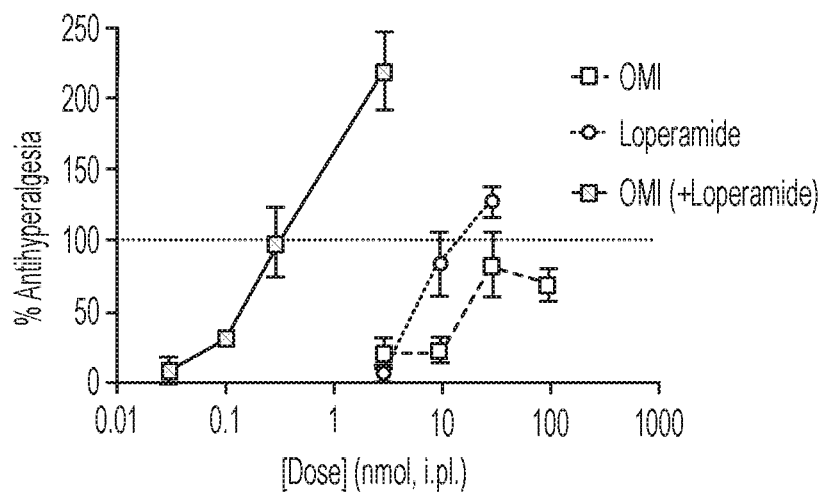
Figure 7D:
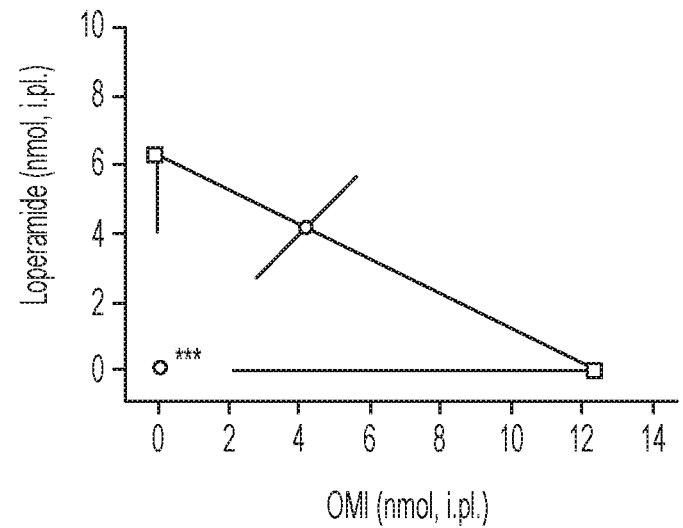

Next, the hypothesis that the peripheral terminals of primary afferents also express both mu-opioid (MOR) and delta-opioid (DOR) receptors, and that loperamide and oxymorphindole synergize behaviorally when administered in the periphery, was tested. Both drugs, as well as the combination, were given as an intraplantar injection in the hindpaw of mice, and thermal nociceptive responses were tested on the Hargreaves assay (Hargreaves, K. et al., *Pain* 32: 77-88, 1988) 15 minutes later. FIG. 7a shows the dose-response curves for loperamide, oxymorphindole and their combination in naïve animals. Following the interaction observed in the spinal cord, the combination ED50 is approximately 10-fold less than either drug alone. The combination ED50 value is 4.59 nmol vs. 57.2 nmol for loperamide and 33.7 nmol for oxymorphindole (n=6 per dose). This shift in potency was statistically synergistic (p<0.01), as demonstrated in FIG. 7b. Next, the ability of intraplantar loperamide and oxymorphindole to synergize in inflamed animals was assessed. Three to five days before testing, animals were given an intraplantar injection of Complete Freund's Adjuvant (CFA) in the left hindpaw, resulting in a robust inflammatory state and hyperalgesic withdrawal thresholds on the Hargreaves assay. Following the confirmation of hyperalgesia, animals were treated with intraplantar drug or combination as previously stated. The dose-response curves for inflamed animals are shown in FIG. 7c. In the inflamed cohort, loperamide and oxymorphindole's ED50 values were 6.37 nmol and 12.3 nmol respectively, while the combination ED50 was 0.1 nmol (n=5 per dose). Therefore, the shift in potency with the combination of drugs is further amplified in an inflammatory state, with approximately a 50-fold difference between individual drug and combination. This too was a statistically significant synergistic interaction (p<0.001), as visualized in FIG. 7d.

Figure 8A:
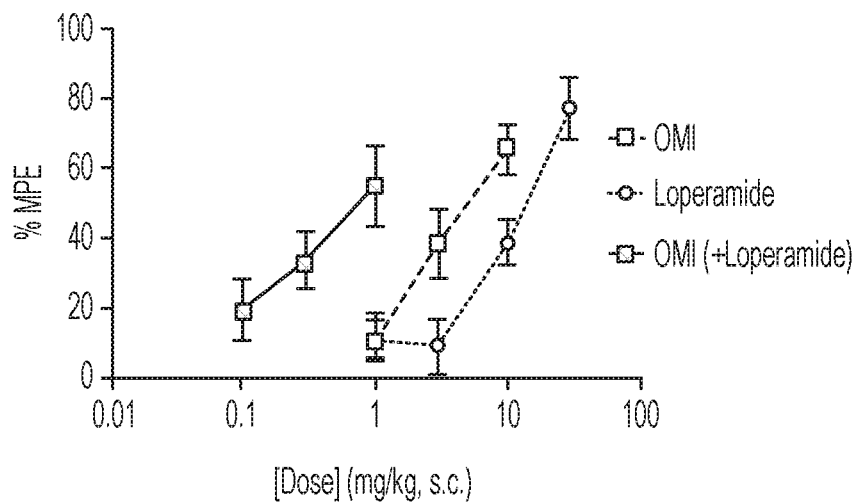
FIGS. 8a-8d show systemically administered OMI-Lo synergizes in naive and inflamed animals.
Figure 8B:
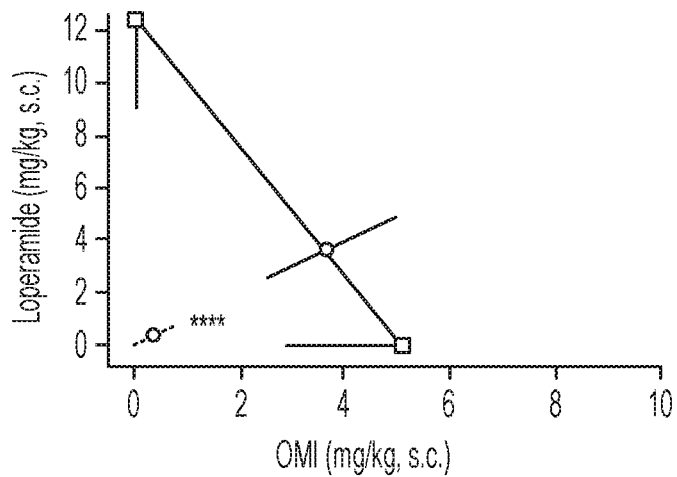
Figure 8C:
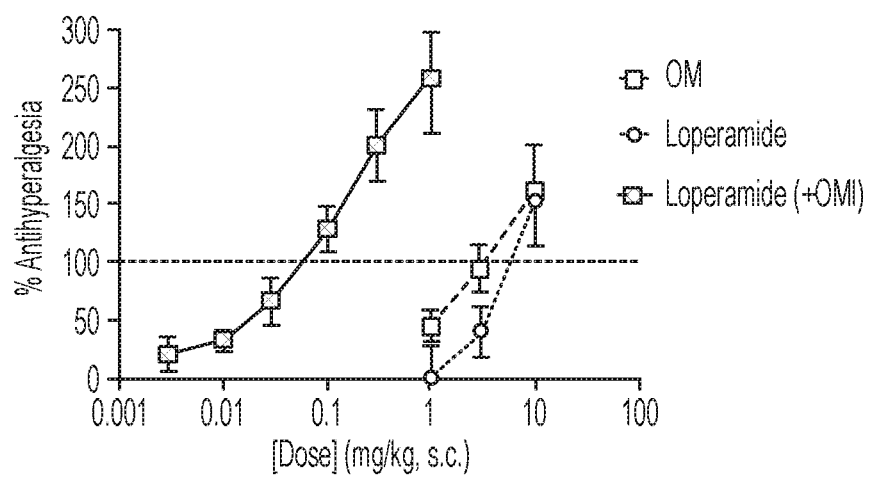
Figure 8D:
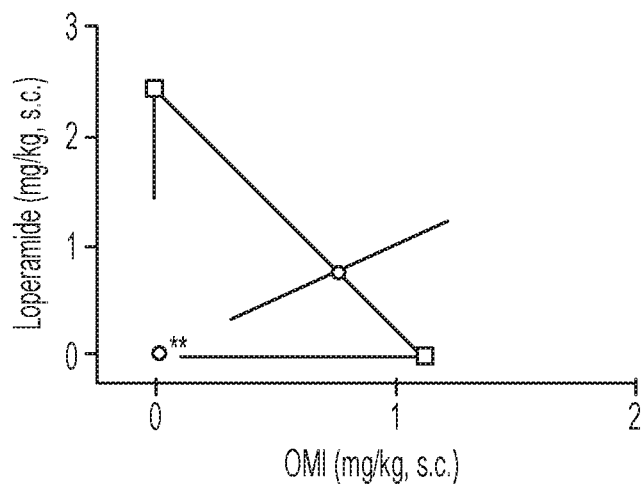
Figure 9A:
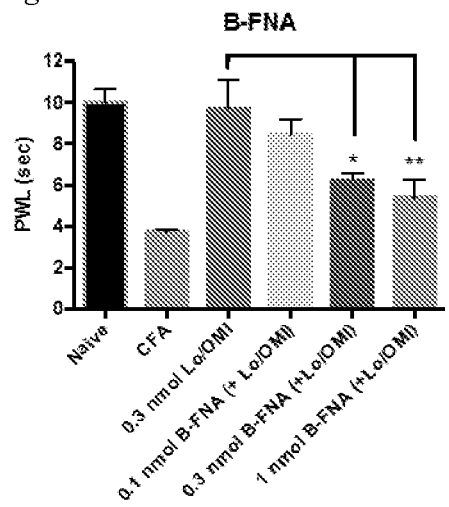
FIGS. 9a-9f show antagonism of locally and systemically-administered OMI-Lo. Paw withdrawal thresholds using the Hargreaves assay were measured for naïve animals, inflamed animals, and animals treated with an intraplantar injection of 0.3 nmol Lo-OMI, or 0.1 mg/kg Lo-OMI.
Figure 9B:
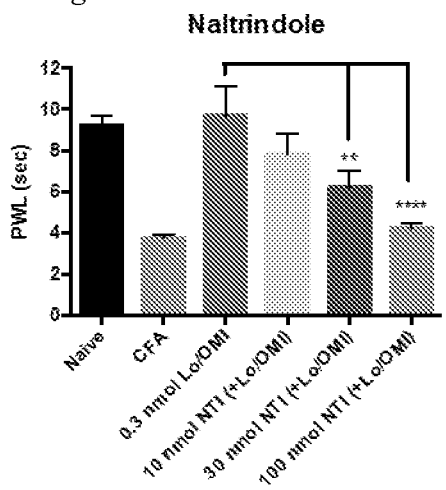
Figure 9C:
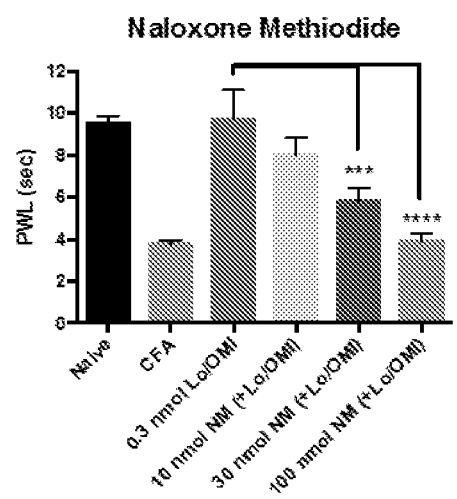
Figure 9D:
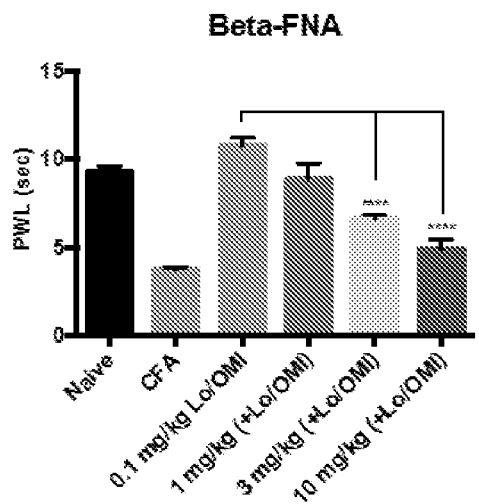
Figure 9E:
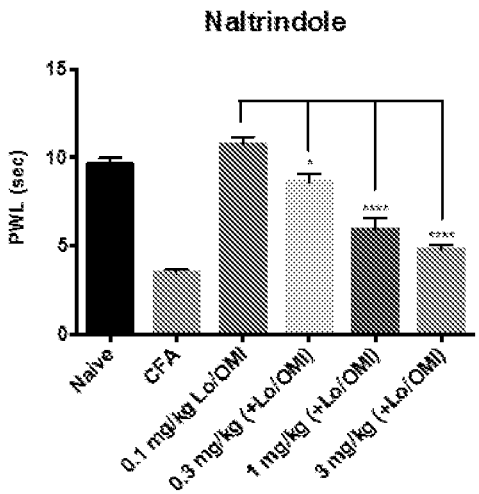
Figure 9F:
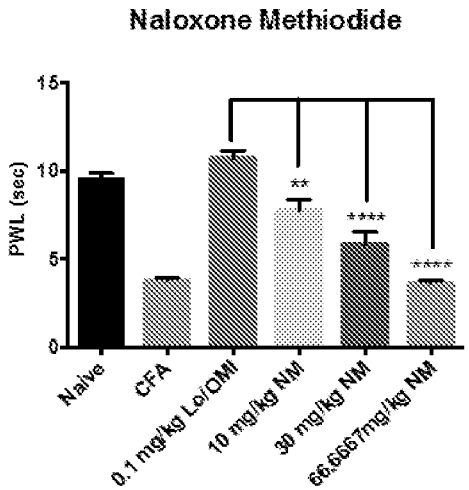

To assess whether systemically administered drugs would exhibit similar behavioral effects, loperamide, oxymorphindole, or combination were given as a subcutaneous injection, and animals were tested on the Hargreaves assay 45 minutes later. FIG. 8a shows the dose-response curves for subcutaneous loperamide, oxymorphindole or their combination in CFA-naïve mice. In this study, the ED50 values were 12.4 mg/kg, 5.13 mg/kg and 0.4 mg/kg for loperamide, oxymorphindole, and their combination, respectively (n=5 per dose), roughly a 10-fold increase in potency. Again, the shift in potency observed for the combination was statistically significant compared to the expected additive combination ED50 (FIG. 8b, p<0.0001). Following the paradigm of the intraplantar study, this protocol was repeated in animals that had been previously inflamed in the hindpaw with CFA. In the inflamed cohort, the observed ED50 values for loperamide, oxymorphindole and combination were 2.42, 1.12, and 0.01 mg/kg respectively, representing a ~100-fold increase in potency. These dose-response curves are shown in FIG. 8c. The isobologram in FIG. 8d demonstrates that the interaction between systemically administered loperamide and oxymorphindole in inflamed mice is also synergistic (p<0.01).

To confirm that the behavioral effects observed in the previous studies were being mediated by action at MORs and DORs, the ability of a panel of opioid antagonists to block the synergism was tested. For this study, naloxone methiodide, a peripherally restricted, pan-opioid receptor antagonist; naltrindole, a DOR-selective antagonist; and beta-funaltrexamine (β-FNA), a MOR-selective antagonist (n=5-6 per dose) were chosen. Naltrindole and naloxone methiodide were co-administered with Lo-OMI. β-FNA was administered 24 hours before the combination. Both intraplantar and subcutaneous administration of antagonists and drugs were tested. All three antagonists significantly reversed the anti-hyperalgesic effects of Lo-OMI in a dose-dependent manner by both routes of administration, as is shown in FIGS. 9a-9f. Importantly, that the peripherally-restricted antagonist, naloxone methiodide, completely ablated the behavioral anti-hyperalgesia confirmed that the synergistic interaction between loperamide and oxymorphindole is mediated by MORs and DORs in the peripheral nervous system, and not in the spinal cord or other supraspinal opioid-targeting regions.

Figure 10A:
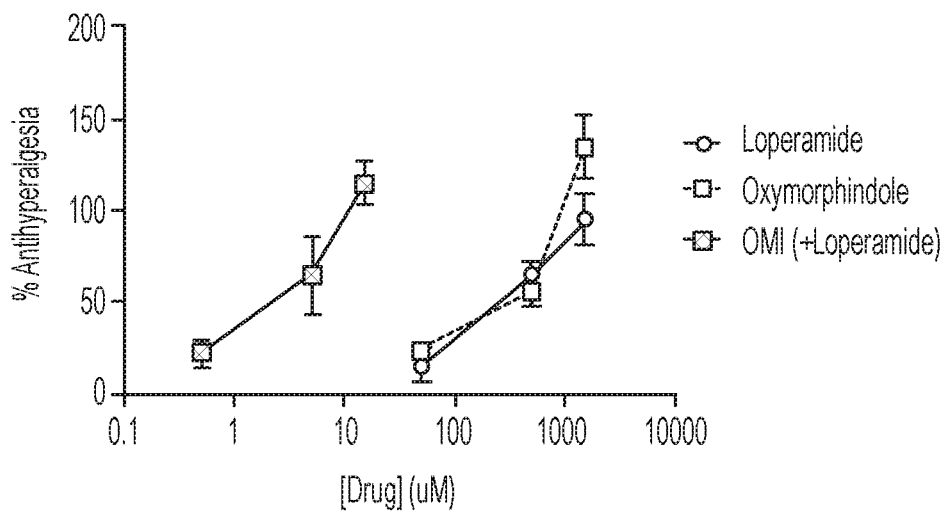
FIGS. 10a and 10b show topically administered OMI-Lo synergizes in CFA-inflamed animals.
Figure 10B:
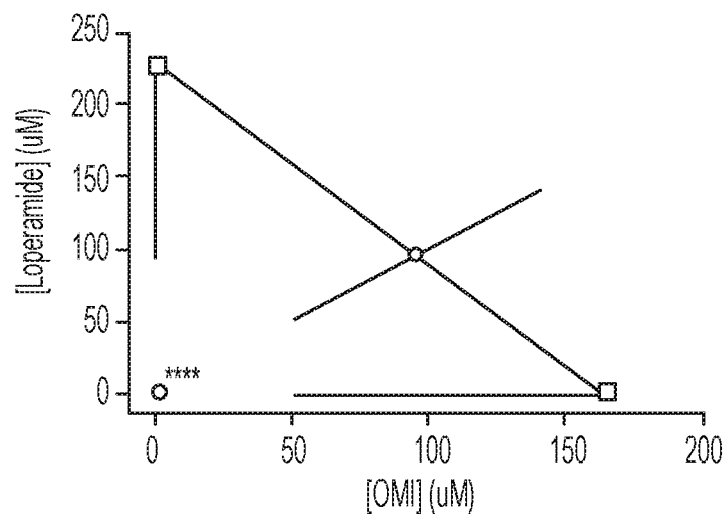
Figure 11A:
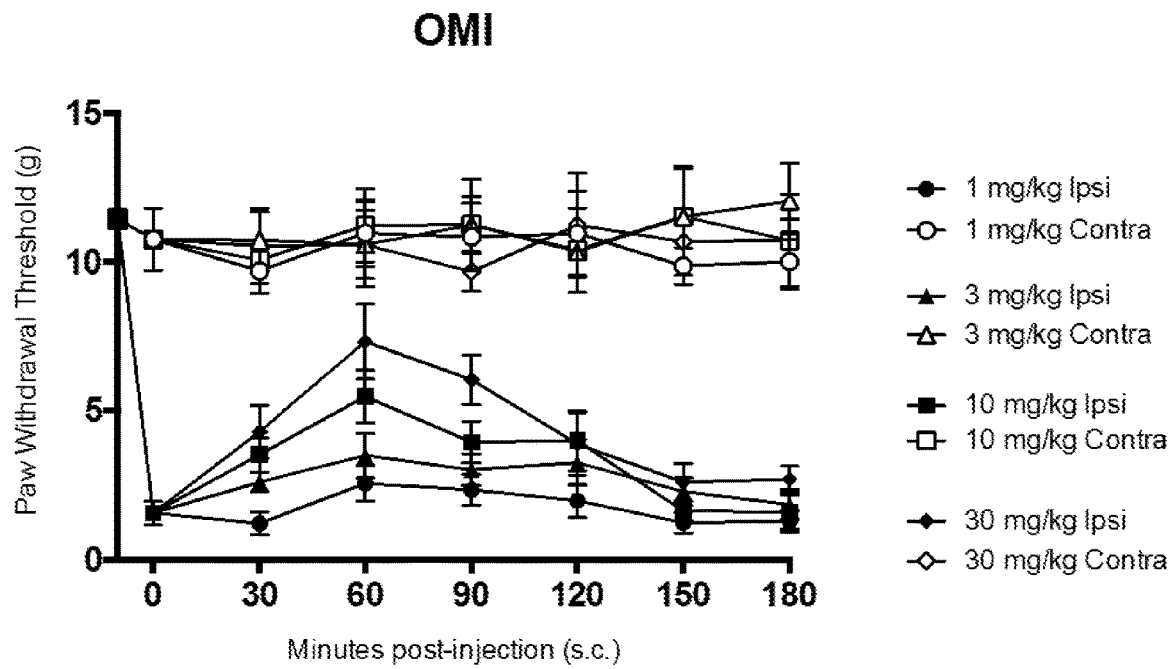
FIGS. 11a-11d show anti-allodynic properties of loperamide, oxymorphindole or combination in nerve-injured animals.
Figure 11B:
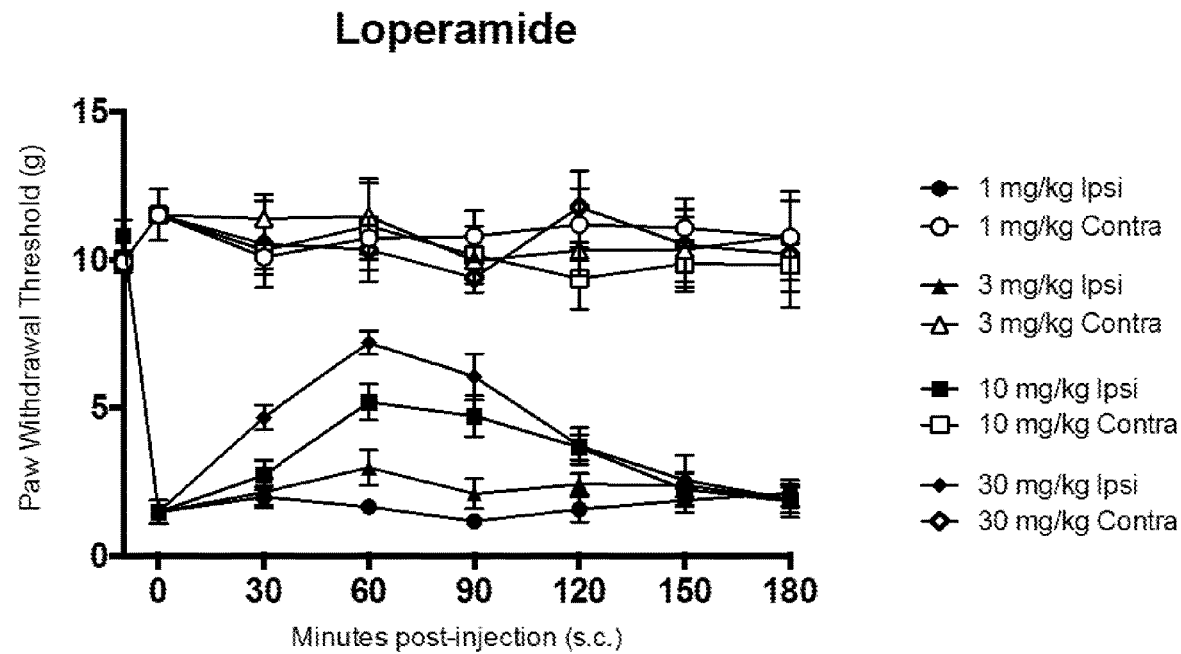
Figure 11C:
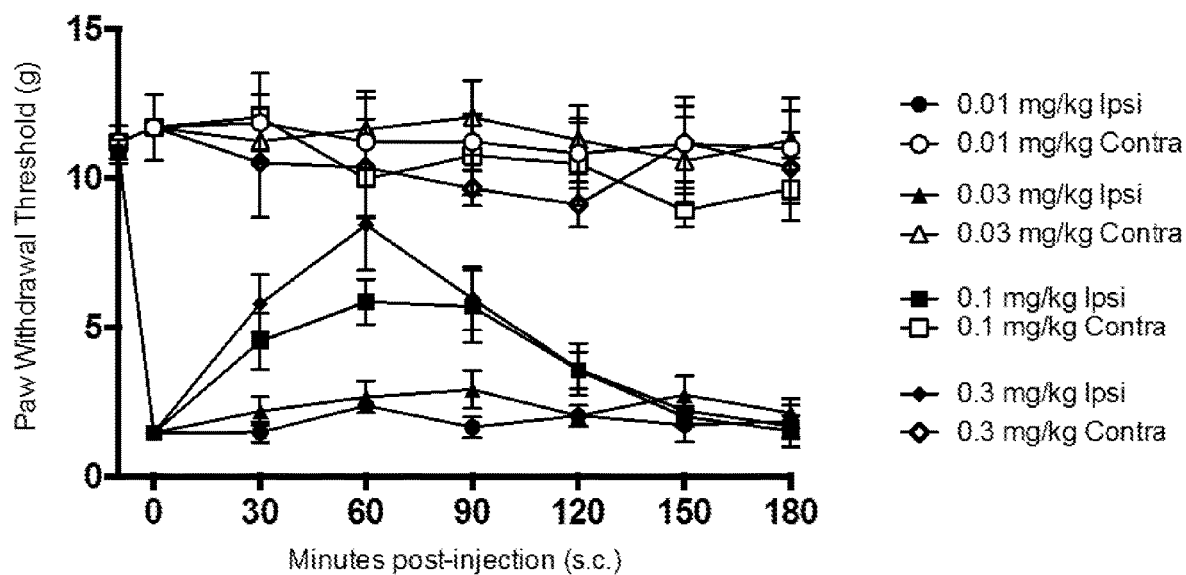
Figure 11D:
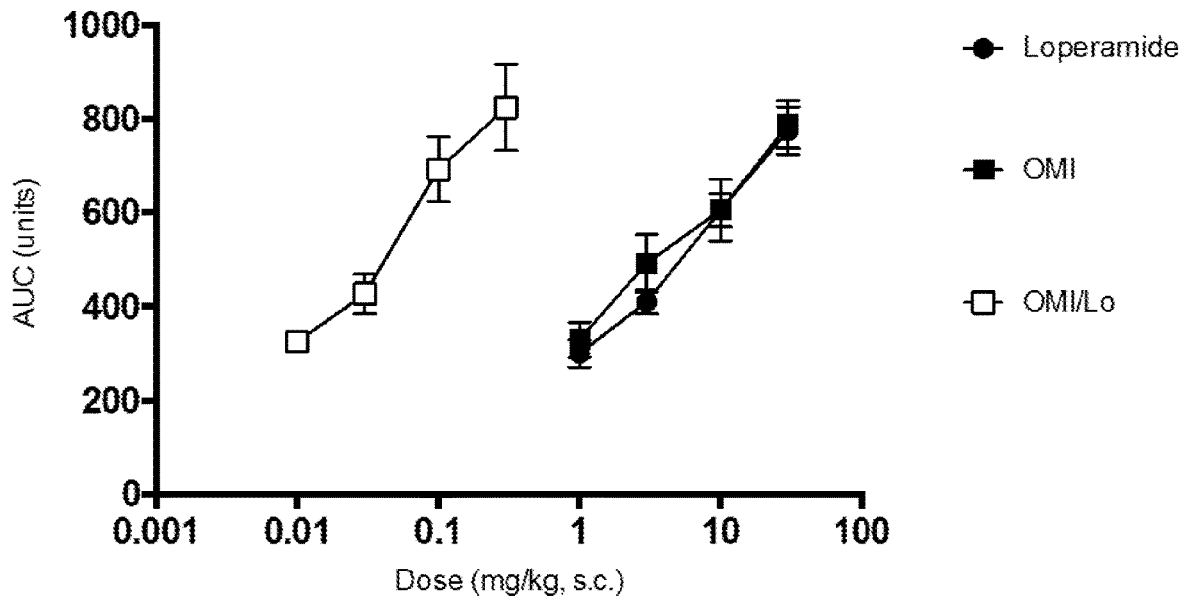

To reinforce the support for the hypothesis that the synergy between loperamide and oxymorphindole is mediated peripherally as opposed to centrally, the drugs were administered alone or in combination as a topical solution to the hindpaws of CFA-inflamed animals, and subsequently thermal nociceptive responses tested on the hyperalgesic hindpaw. As shown in FIG. 10a, loperamide and oxymorphindole showed similar potency as topical solutions, with ED50 values in this assay of 227 and 166 micromolar respectively. When combined, the shift in potency was comparable to the intraplantar administration, with a combination ED50 of 1.72 micromolar, which corresponds to an approximately 100-fold shift in potency. This interaction was determined to be statistically significantly synergistic by isobolographic analysis (p<0.0001), as shown in FIG. 10b.

After establishing the anti-hyperalgesic effects of systemic, peripheral, and topical loperamide and oxymorphindole in CFA-inflamed animals, we sought to determine whether the synergistic analgesia generalizes to other types of injury. First, a neuropathic pain state was induced in a cohort of animals using the spared nerve injury (SNI) model, which induces a robust mechanical allodynia in the affected hindpaw lasting for weeks (DeCosterd I. and Woolf C. J., *Pain* 87: 149-158, 2000). Ten-14 days after surgery, when the neuropathic state has been established, the animals were given a subcutaneous injection of loperamide, oxymorphindole or their combination, and their mechanical paw withdrawal thresholds were measured using an electronic von Frey apparatus. Both loperamide and oxymorphindole, as well as the combination, transiently reversed the neuropathic allodynia in a dose-dependent manner. The anti-allodynic effect peaked at sixty minutes post-injection, and paw withdrawal thresholds returned to baseline after three hours. Using area under the curve as a measure of dose dependence, the combination of loperamide and oxymorphindole was again 100 times more potent than either drug alone. These data are presented in FIGS. 11a-11d. It is concluded from these data that the synergy between these two compounds is not restricted to naïve or inflammatory states.

Figure 12:
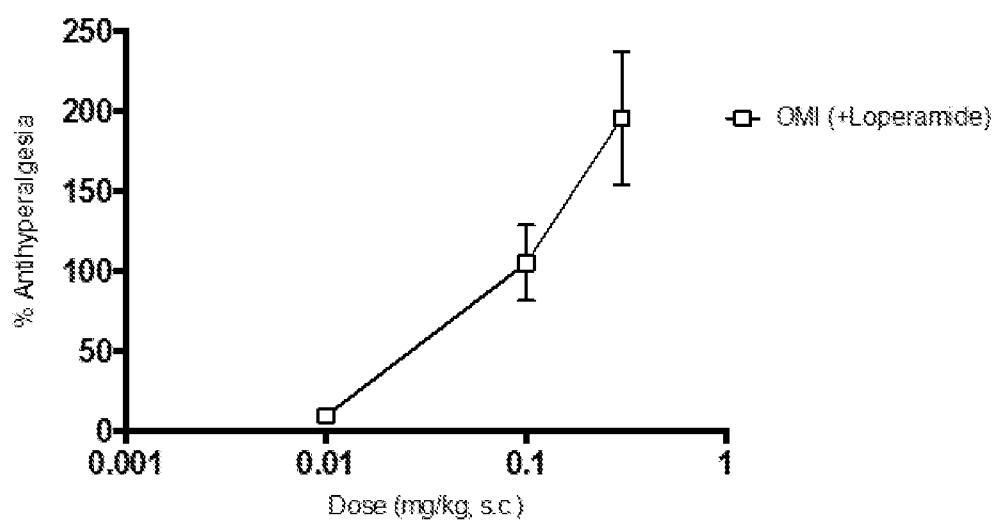
FIG. 12 shows Lo-OMI is effective in reversing post-operative pain in mice Animals (n=6 per dose) were subjected to a paw incision surgery, which results in a robust thermal hyperalgesia 3 hours after surgery, and lasts for 3 days. 24 hours after surgery, animals were given a subcutaneous injection of Lo-OMI, and their paw withdrawal reflexes were measure on the Hargreaves assay. Data are analyzed as a % anti-hyperalgesia.

To test the combination's anti-hyperalgesic properties in a post-operative pain model (Brennan. T. J. et al., *Pain* 64.3 (1996): 493-502), animals were subjected to a paw incision surgery, which resulted in a thermal hyperalgesia as early as three hours post-surgery as measured by the Hargreaves assay. One day after surgery, animals were given subcutaneous injections of Lo-OMI, and retested on the Hargreaves apparatus. FIG. 12 shows the dose-response curve for the combination in this model, with efficacy and potency mirroring what was observed for subcutaneous administration in our CFA-induced inflammatory pain model.

Figure 13A:
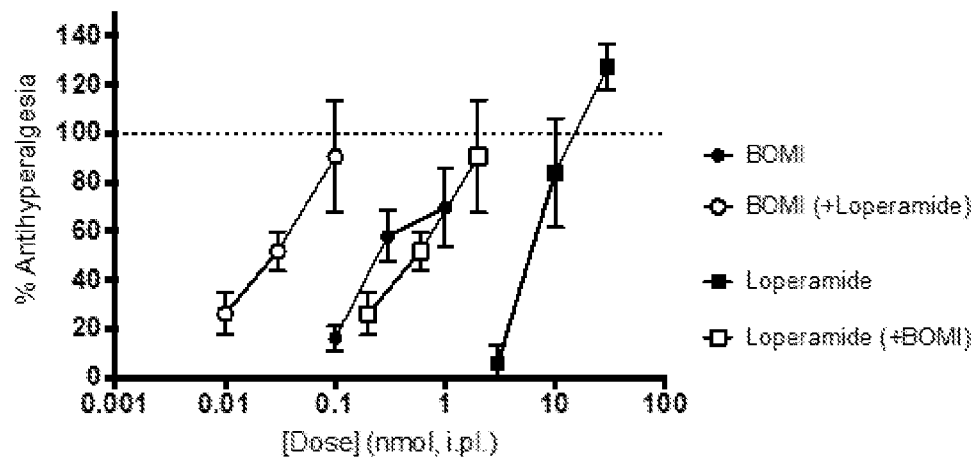
FIGS. 13a-13d show loperamide and BOMI synergize in inflammatory pain states.
Figure 13B:
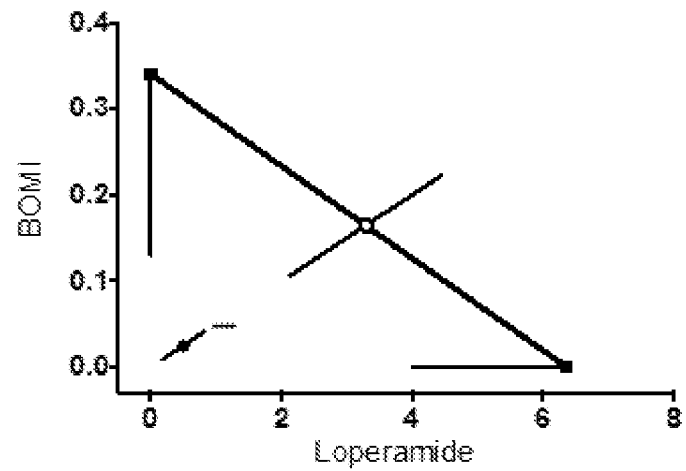
Figure 13C:
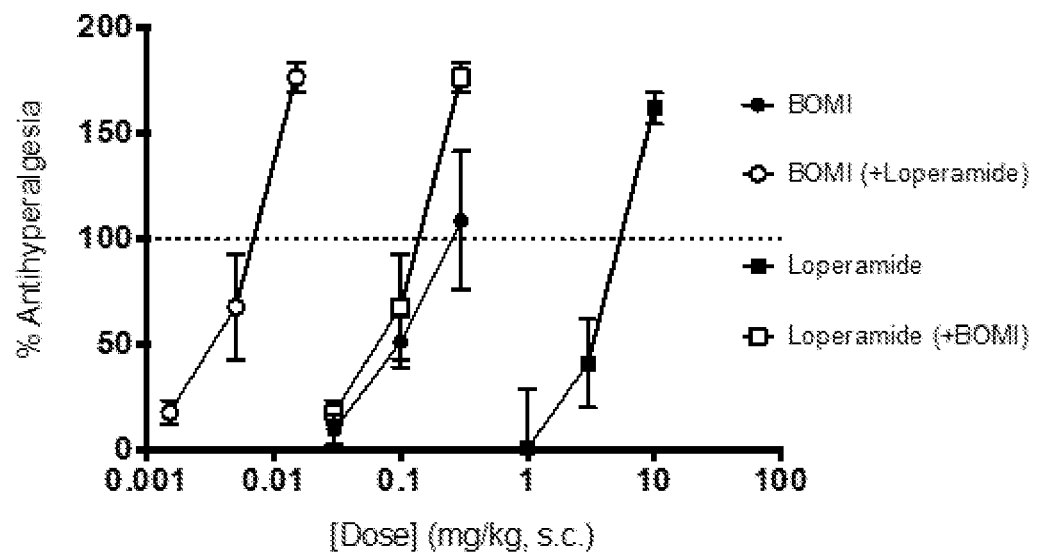
Figure 13D:
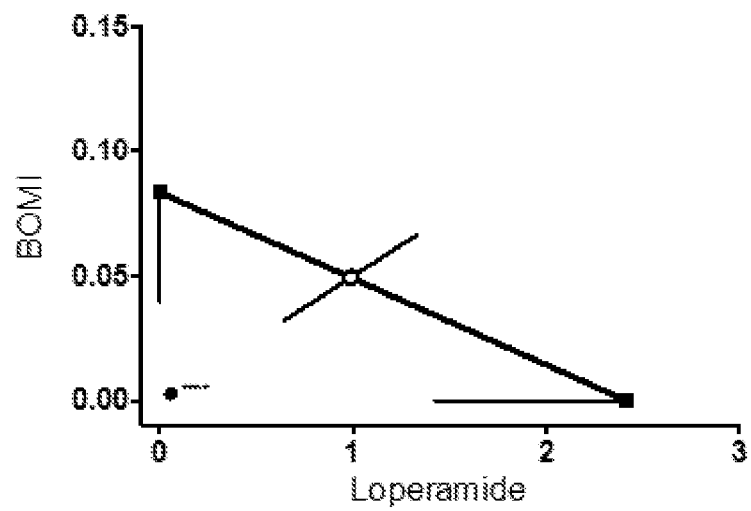

Finally, we tested whether a DOR agonist analogue of oxymorphindole, N-benzyloxymorphindole (BOMI), would also participate as a synergistic agonist with loperamide. The local and systemic injection paradigms were tested for loperamide, BOMI, and combination in the CFA-induced inflammatory pain model, and the resulting dose-response curves and isobolograms are shown in FIG. 13*a*-13*d*. For the intraplantar administration, the ED50 values for loperamide, BOMI alone were 6.37 nmol and 0.34 nmol respectively. The ED50 for loperamide when BOMI is also present is 0.5 nmol, and the ED50 for BOMI when loperamide is also present is 0.02 nmol. The corresponding dose-response curves are shown in FIG. 13*a*. These values represent a ~10-fold shift in potency, which was statistically significant when analyzed for the isobologram (p<0.0001, FIG. 13*b*). When the drugs were given systemically, the ED50 values for loperamide and BOMI alone were 2.42 mg/kg and 0.08 mg/kg, respectively. When co-administered, the ED50 for loperamide with BOMI present was 0.06 mg/kg, and the ED50 for BOMI with loperamide present was 0.003 mg/kg. The systemic dose-response curves are shown in FIG. 13*c*. Again, this 30-fold shift in potency was statistically significant (p<0.0001, FIG. 13*d*).

To determine whether the combination of loperamide and oxymorphindole demonstrated adverse side effects, such as motor impairment, animals were trained to walk on an accelerating rotarod apparatus for a five minute period of time. Once the mice are able to demonstrate their ability to remain on the rotarod and walk for the five minute period, they received a drug injection. Following drug exposure, they are subsequently observed for their ability to walk on the rotating rod. This task tests for drug-induced motor impairment and/or sedation.

Figure 14:
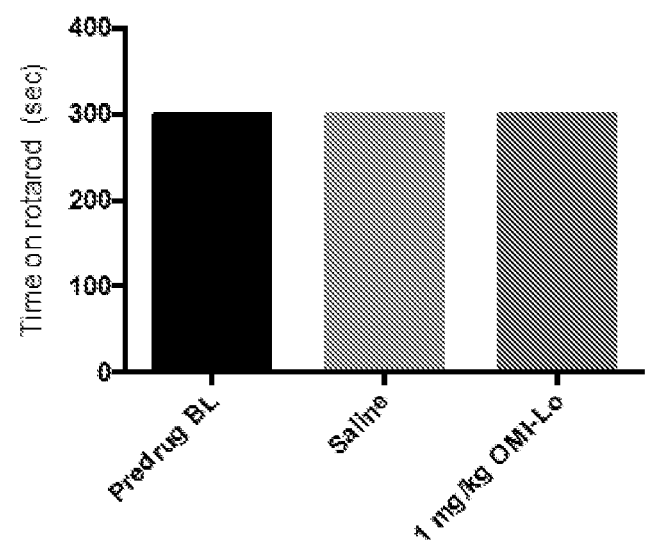
FIG. 14 shows assessment of motor impairment. After three training sessions, mice walked for 300 s on an accelerating (4-40 rpm) rotarod (Ugo Basile, Varese, Italy). All subjects were able to remain on the rotating rod for the duration of the five minute period.

It has been previously demonstrated that the accelerating rotarod assay used is a sensitive measure of motor impairment and sedation. For example, intrathecal MK801, known to result in motor impairment, results in an 80% reduction in rotarod performance with an ED50 value of 11 nmol (6.3-18) (Fairbanks, C. A. et al, *PNAS* 97.19 (2000): 10584-10589). More recent studies with intravenously delivered MK801 (0.25 mg/kg) also results in significant reduction in the rotarod assay in nerve-injured mice (Fairbanks, unpublished results). Additionally, intrathecal or systemic clonidine (known to be sedative) dose-dependently and fully impairs rotarod performance. Morphine delivered either intrathecally or systemically resulted in a significant and dose-related (albeit partial) impairment of motor function (Stone, L. S. et al., *PloS One* 9.10 (2014): e109903). In the present study, after subjects were trained to perform the rotatord task, an intravenous injection of either saline or 1 mg/kg Lo-OMI was given and were retested after 15 minutes. Neither the Lo-OMI group nor the saline group showed inhibition of rotarod performance (FIG. 14). In other words, they were able to complete the walking task for the full five minute period of time. Therefore, it has shown that Lo-OMI does not induce motor impairment.

CONCLUSIONS

Experiments in mice have shown that a 1:1 dose ratio with either locally (intraplantar injection, i.pl.) or systemically (subcutaneous injection, s.c.), oxymorphindole-loperamide (OMI-Lo) produces analgesia at 4- to 10-fold lower doses (naïve subjects) or antihyperalgesia at 50-100-fold lower doses (subjects injected i.pl. with Freund's complete adjuvant (CFA) 3-5 days earlier) than either agent given alone. That is, the MOR agonist significantly synergizes with the DOR agonist at peripheral sites of action, providing a peripherally directed combination opioid analgesic therapy with very low abuse liability to human use. Importantly, the high potency of OMI-Lo generalizes from the inflammatory model (CFA) to both neuropathic (SNI) and post-operative (incisional) models in rodent; the combination treatment therefore promises broad applicability to the management of persistent pain in patients.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition suitable for administration by injection, oral administration, or topical administration, comprising 1) a 1:1 ratio of loperamide and oxymorphindole, and 2) a pharmaceutically acceptable carrier.

2. A method for treating pain in an animal comprising administering a 1:1 ratio of loperamide, and oxymorphindole to the animal by injection, oral administration, or topical administration.

* * * * *